(12) United States Patent
Rapp

(10) Patent No.: US 7,176,300 B2
(45) Date of Patent: Feb. 13, 2007

(54) AVIAN LYSOZYME PROMOTER

(75) Inventor: Jeffrey C. Rapp, Athens, GA (US)

(73) Assignee: AviGenics, Inc., Athens, GA (US)

( * ) Notice: Subject to any disclaimer, the term of this patent is extended or adjusted under 35 U.S.C. 154(b) by 0 days.

(21) Appl. No.: 09/922,549

(22) Filed: Aug. 3, 2001

(65) Prior Publication Data

US 2002/0199214 A1 Dec. 26, 2002

Related U.S. Application Data

(60) Provisional application No. 60/280,004, filed on Mar. 30, 2001.

(51) Int. Cl.
C07H 21/04 (2006.01)
C12N 15/00 (2006.01)
C12N 5/06 (2006.01)

(52) U.S. Cl. ............... 536/24.1; 536/23.5; 536/24.1; 435/320.1

(58) Field of Classification Search ............. 435/69.1, 435/69.7, 320.1, 252.3, 325, 455; 536/23.1, 536/24.1
See application file for complete search history.

(56) References Cited

U.S. PATENT DOCUMENTS

| | | | |
|---|---|---|---|
| 4,237,224 | A | 12/1980 | Cohen et al. |
| 4,603,112 | A | 7/1986 | Paoletti et al. |
| 4,722,848 | A | 2/1988 | Paoletti et al. |
| 4,769,330 | A | 9/1988 | Paoletti et al. |
| 5,174,993 | A | 12/1992 | Paoletti et al. |
| 5,175,384 | A | 12/1992 | Krimpenfort et al. |
| 5,338,683 | A | 8/1994 | Paoletti et al. |
| 5,494,807 | A | 2/1996 | Paoletti et al. |
| 5,505,941 | A | 4/1996 | Paoletti et al. |
| 5,580,859 | A | 12/1996 | Felgner et al. |
| 5,589,466 | A | 12/1996 | Felgner et al. |
| 5,591,639 | A | 1/1997 | Bebbington |
| 5,731,178 | A | 3/1998 | Sippel et al. |
| 6,730,822 | B1 * | 5/2004 | Ivarie et al. ............. 800/19 |

FOREIGN PATENT DOCUMENTS

| | | |
|---|---|---|
| WO | WO 91/06309 | 11/1989 |
| WO | WO 92/06180 | 10/1990 |
| WO | WO 92/19749 | 5/1991 |
| WO | WO 92/20316 | 5/1991 |
| WO | WO 92/22635 | 6/1991 |
| WO | WO 93/04701 | 9/1991 |
| WO | WO 93/25234 | 6/1992 |
| WO | WO 94/06920 | 9/1992 |
| WO | WO 94/11524 | 11/1992 |
| WO | WO 97/47739 | 6/1996 |
| WO | WO 99/19472 | 10/1997 |
| WO | WO 00/11151 | 8/1998 |
| WO | WO 00/56932 | 3/1999 |

OTHER PUBLICATIONS

Alberts, Bray, Lewis, Raff, Roberts and Watson. 1994. Molecular Biology of the Cell. Garland Publishing, New York and London. pp. 5-6, 227, 341.*
Wagstrom, Yoon and Zimmerman. 2000. Immune Components in Porcine Mammary Secretions. Viral Imm. 13(3):383-397.*
Renkawitz R, Schutz G, von der Ahe D, Beato M. Sequences in the promoter region of the chicken lysozyme gene required for steroid regulation and receptor binding. 1984. Cell.37(2):503-10.*
Grewal T et al. The -6.1-kilobase chicken lysozyme enhancer is a multifactorial complex containing several cell-type specific elements. 1992. Mol Cell Biol. 12(5):2339-50.*
Stumph WE, Hodgson CP, Tsai MJ, O'Malley BW. Genomic structure and possible retroviral origin of the chicken CR1 repetitive DNA sequence family.1984. Proc Natl Acad Sci U S A. 81(21):6667-71.*
Chloramphenicol acetyl transferase search result. Bio Tech Life Science on-line Dictionary. Jun. 12, 2006. p. 1 of 1.*
Exons encode functional and structural units of chicken lysozyme, Jung et al; PNAS USA, 77:5759-5763, (Oct. 1980).
An Initiation Zone of Chromosomal DNA Replication at the Chicken Lysozyme Gene Locus*, Loc Phi-van et al; The Journal of Biological Chemistry 274:18300-18307 (1998).
The matrix attachment regions of the chicken lysozyme gene co-map with the boundaries of the chromatin domain, Phi-Van and Stratling; EMBO Journal 7:655-664 (1988).
Lysozme Level in Blood Serum of Newly Hatched White Leghorn Chickens, Rosolowska-Huszcz; Bulletin De L'academie Polonaise Des Sciences, 26:891-894 (1978).
Prerequisites for tissue specific and position independent expression of a gene locus in transgenic mice, Bonifer et al; J Mol Med 74:663-671(1996).

(Continued)

Primary Examiner—Daniel M. Sullivan
Assistant Examiner—Laura McGillem
(74) Attorney, Agent, or Firm—Kyle D. Yesland

(57) ABSTRACT

The invention provides for lysozyme gene expression control regions which may include a 5' matrix attachment region; an intrinsically curved region of DNA; a transcription enhancer; a negative regulatory element; at least one hormone responsive element; an avian CRI repeat element; a proximal lysozyme promoter, and can be linked to a nucleotide sequence encoding a heterologous polypeptide.

34 Claims, 16 Drawing Sheets

OTHER PUBLICATIONS

A nuclear DNA attachment element mediates elevated and position-independent gene activity, Stief et al; Nature 341:343-345(Sep. 1989).

Tissue specific and position independent expression of the complete gene domain for chicken lysozyme in transgenic mice, Bonifer et al; EMBO Journal 9:2843-2848 (1990).

Stopped at the border: boundaries and insulators, Bell and Felsenfeld; Current Opinion in Genetics & Development,9:191-198(1999).

Dissection of the Ability of the Chicken Lysozyme Gene 5' Matrix Attachment Region To Stimulate Transgene Expression and To Dampen Position Effects; Phi-Van and Stratling; Biochemistry 35:10735-10742(1996).

Activity of two different silencer elements of the chicken lysozyme gene can be compensated by enhancer elements, Baniahmad et al; EMBO Journal 6:2297-2303(1987).

The lysozyme enhancer: cell-specific activation of the chicken lysozyme gene by far-upstream DNA element, Theisen et al; EMBO Journal 5:719-724(1986).

The Chicken Lysozyme Locus as a Paradigm for the Complex Developmental Regulation of the Eukaryotic Gene Loci, Bonifer et al; Journal of Biological Chemistry 272:26075-26078(1997).

A progesterone responsive element maps to the far upstream steroid dependent DNase hypersensitive site of chicken lysozyme chromatin, Hecht et al; EMBO Journal 7:2063-2073(1988).

Chromatin fine structure profiles for a developmentally regulated gene: reorganization of the lysozyme locus before trans-activator binding and gene expression, Kontaraki et al.; Genes & Development 14:210 2122(2000).

The Far Upstream Chicken Lysozyme Enhancer at-6.1 Kilobase, by Interacting with NF-M, Mediates Lipopolysaccharide-induced Expression of the Chicken Lysozyme Gene in Chicken Myelomonocytic Cells, Goethe and Phi Van; Journal of Biological Chemistry 269:31302-31309(1994).

Chromatin Domains Constitute Regulatory Units for the Control of Eukaryotic genes, Sippel et al;Cold Spring Harbor Symposia on Quantitative Biology, 58:37-44(1993).

Dynamic Changes in the Chromatin of the Chicken Lysozyme Gene Domain During Differentiation of Multipotent Progenitors to Macrophages, Huber et al; DNA and Cell Biology 14:397-402(1995).

Alternative sets of DNase I-hypersensitive sites characterize the various functional states of the chicken lysozyme gene, Fritton et al; Nature 311:163-165(Sep. 1984).

Reduced Position Effect in Mature Transgenic Plants conferred by the Chicken Lysozyme Matrix-Associated Region, Mlynarova et al;The Plant Cell 6:417-426(1994).

Development of position-independent expression vectors and their transfer into transgenic fish, Caldovic and Hackett; Mol. Marine Biol. and Biotech 4:51-61(1995).

Chicken repeat 1(CR1) elements, which define an ancient family of vertebrate non-LTR retrotransposons, contain two closely spaced open reading frames, Haas et al; Gene 197:305-309(1997).

Sequence conservation in avian CR1: An interspersed repetitive DNA family evolving under functional constraints, Chen et al; PNAS USA 88:5814-5818 (Jul. 1991).

Position-independent expression of transgenes in zebrafish, Caldovic et al; Transgenic Research 8:321-334(1999).

Lysozyme in Hen Blood Serum, Sato and Watanabe, Poultry Science 55:1749-1756(1976).

Untitled, Steiner et al; Nucleic Acids Research, 15:4163-4178 (1987).

* cited by examiner

SpLMAR2
TGCCGCCTTCTTTGATATTC            SEQ ID NO: 1

LE-6.1kbrev1
TTGGTGGTAAGGCCTTTTTG            SEQ ID NO: 2

Lys-6.1
CTGGCAAGCTGTCAAAAACA            SEQ ID NO: 3

LysE1rev
CAGCTCACATCGTCCAAAGA            SEQ ID NO: 4

LYSBSU
CCCCCCCCTAAGGCAGCCAGGGGCAGGAAGCAAA   SEQ ID NO: 5

SalItoNotI
TCGAGCGGCCGC                    SEQ ID NO: 6

T7
TAATACGACTCACTATAGGG            SEQ ID NO: 7 lys61enfor1
CGTGGTGATCAAATCTTTGTG           SEQ ID NO: 8 lys61enrev1
AGGAGGGCACAGTAGGGATC            SEQ ID NO: 9

5MARfor1
GTGGCCTGTGTCTGTGCTT             SEQ ID NO: 10

IFN-3rev
AACTCCTCTTGAGGAAAGCC            SEQ ID NO: 11 lys001rev
TCCTGTTTGGGATGAATGGT            SEQ ID NO: 12 lys002for
CTCTCAGAATGCCCAACTCC            SEQ ID NO: 13 lys003for
TGTATTGGTCTCCCTCCTGC            SEQ ID NO: 14 lys005for
TGTTGAAATTGCAGTGTGGC            SEQ ID NO: 15 lys006rev
TGACAATGCAAATTTGGCTC            SEQ ID NO: 16

*Fig. 1a* lys007for
GATATCCTTGCAGTGCCCAT                      SEQ ID NO: 17 lys008rev
GGACAAGCAAGTGCATCAGA                      SEQ ID NO: 18 lys009for
CTGATGTGCTTCAGCTCTGC                      SEQ ID NO: 19 lys010rev
TCCATGGTGGTCAAACAGAA                      SEQ ID NO: 20 lys011for
GTACTAGACCAGGCAGCCCA                      SEQ ID NO: 21 lys012rev
GTGGGAAGTACCACATTGGC                      SEQ ID NO: 22 lys013for
CGCTCAGGAGAAAGTGAACC                      SEQ ID NO: 23 lys014rev
CGGTTTTGCCTTTGTGTTTT                      SEQ ID NO: 24 lys015rev
AAATGCTCGATTTCATTGGG                      SEQ ID NO: 25 lys016rev
GCCAATCAGACTGCATTTCA                      SEQ ID NO: 26 lys017rev
AACCGCTGAATGGAACAGTC                      SEQ ID NO: 27 lys018for
ACACGCACATATTTTGCTGG                      SEQ ID NO: 28 lys019rev
CAGGAGCTGGATTCCTTCAG                      SEQ ID NO: 29 lys020for
AAAGGATGCAGTCCCAAATG                      SEQ ID NO: 30 lys021rev
GCCCCTAGACTCCATCTTCC                      SEQ ID NO: 31 lys022rev
ATTTGCTGTGGTGGATGTGA                      SEQ ID NO: 32

*Fig. 1b*

| | | |
|---|---|---|
| lys024for<br>CCTTGCAGTCCTTGGTTTGT | | SEQ ID NO: 33 |
| lys025rev<br>ATGATCCTTCTGATGGGCTG | | SEQ ID NO: 34 |
| lys026rev<br>ACAGTGATAGCACAAGGGGG | | SEQ ID NO: 35 |
| lys027rev<br>GTAAACAGCTGCAACAGGCA | | SEQ ID NO: 36 |
| lys028rev<br>CAACACAAAAGTTGGACAGCA | | SEQ ID NO: 37 |
| lys029rev<br>TTTGCAGATGAGACGTTTGC | | SEQ ID NO: 38 |
| lys030rev<br>CCACAAGTTCTTGTTTGGGC | | SEQ ID NO: 39 |
| lys031rev<br>ATCAATCCATGCCAGTAGCC | | SEQ ID NO: 40 |
| lys032rev<br>GTTTAAGGCCCCTTCCAATC | | SEQ ID NO: 41 |
| lys033for<br>GAGAGGGGGTTGGGTGTATT | | SEQ ID NO: 42 |
| lys034for<br>ACAGTGGAAGCATTCAAGGG | | SEQ ID NO: 43 |
| lys037for<br>CCAATGCCTTTGGTTCTGAT | | SEQ ID NO: 44 |
| lys038for<br>AAAACACAAAGGCAAAACCG | | SEQ ID NO: 45 |
| lys039rev<br>CTAAGCCTCGCCAGTTTCAA | | SEQ ID NO: 46 |
| lys040rev<br>TGCCATGAAAACCCTACTGA | | SEQ ID NO: 47 |
| lys041for<br>GGAATGTACCCTCAGCTCCA | | SEQ ID NO: 48 |

*Fig. 1c*

| | | |
|---|---|---|
| lys042rev<br>CCTCTTTAGGAGGCCAGCTT | | SEQ ID NO: 49 |
| lys043rev<br>AAGATGATCAGAGGGCTGGA | | SEQ ID NO: 50 |
| lys044rev<br>GCAGCGCTGGTAATCTTCAT | | SEQ ID NO: 51 |
| lys045for<br>CTTCAGATCCCAGGAAGTGC | | SEQ ID NO: 52 |
| lys046for<br>TTCCTGCCTTACATTCTGGG | | SEQ ID NO: 53 |
| lys047for<br>CCCACTGCAGGCTTAGAAAG | | SEQ ID NO: 54 |
| lys048for<br>AGTTCTCCATAGCGGCTGAA | | SEQ ID NO: 55 |
| lys051for<br>TGCATCCTTCAGCACTTGAG | | SEQ ID NO: 56 |
| lys052rev<br>GCAGGAGGGAGACCAATACA | | SEQ ID NO: 57 |
| lys053for<br>TGCACAAGGATGTCTGGGTA | | SEQ ID NO: 58 |
| lys054for<br>TCCTAGCAACTGCGGATTTT | | SEQ ID NO: 59 |
| lys056for<br>TCTTCCATGTTGGTGACAGC | | SEQ ID NO: 60 |
| lys058for<br>CCCCCTTGTGCTATCACTGT | | SEQ ID NO: 61 |
| lys059for<br>CTGACAGACATCCCAGCTCA | | SEQ ID NO: 62 |
| lys060for<br>AAGTTGTGCTTCTGCGTGTG | | SEQ ID NO: 63 |
| lys061for<br>TTGTTCCTGCTGTTCCTCCT | | SEQ ID NO: 64 |

*Fig. 1d*

SEQ ID NO: 65

```
TGCCGCCTTC TTTGATATTC ACTCTGTTGT ATTTCATCTC TTCTTGCCGA TGAAAGGATA   60
TAACAGTCTG TATAACAGTC TGTGAGGAAA TACTTGGTAT TTCTTCTGAT CAGTGTTTTT  120
ATAAGTAATG TTGAATATTG GATAAGGCTG TGTGTCCTTT GTCTTGGGAG ACAAAGCCCA  180
CAGCAGGTGG TGGTTGGGGT GGTGGCAGCT CAGTGACAGG AGAGGTTTTT TTGCCTGTTT  240
TTTTTTTTTT TTTTTTTTTT AAGTAAGGTG TTCTTTTTTC TTAGTAAATT TTCTACTGGA  300
CTGTATGTTT TGACAGGTCA GAAACATTTC TTCAAAAGAA GAACCTTTTG GAAACTGTAC  360
AGCCCTTTTC TTTCATTCCC TTTTGCTTT CTGTGCCAAT GCCTTGGTT CTGATTGCAT  420
TATGGAAAAC GTTGATCGGA ACTTGAGGTT TTATTTATA GTGTGGCTTG AAAGCTTGGA  480
TAGCTGTTGT TACACGAGAT ACCTTATTAA GTTTAGGCCA GCTTGATGCT TTATTTTTC  540
CCTTTGAAGT AGTGAGCGTT CTCTGGTTTT TTTCCTTTGA AACTGGTGAG GCTTAGATTT  600
TTCTAATGGG ATTTTTTACC TGATGATCTA GTTGCATACC CAAATGCTTG TAAATGTTTT  660
CCTAGTTAAC ATGTTGATAA CTTCGGATTT ACATGTTGTA TATACTTGTC ATCTGTGTTT  720
CTAGTAAAAA TATATGGCAT TTATAGAAAT ACGTAATTCC TGATTTCCTT TTTTTTATC  780
TCTATGCTCT GTGTGTACAG GTCAAACAGA CTTCACTCCT ATTTTATTT ATAGAATTTT  840
ATATGCAGTC TGTCGTTGGT TCTTGTGTTG TAAGGATACA GCCTTAAATT TCCTAGAGCG  900
ATGCTCAGTA AGGCGGGTTG TCACATGGGT TCAAATGTAA ACGGGCACG TTTGGCTGCT  960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGGAAATA CACTGACTTG ATTGAAGTCT CTTGAAGATA GTAAACAGTA 1620
CTTACCTTTG ATCCCAATGA AATCGAGCAT TCAGTTGTA AAAGAATTCC GCCTATTCAT 1680
ACCATGTAAT GTAATTTTAC ACCCCAGTGT CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAAA 1920
AAAAAAAAAG TAATATAAAA AGGACCAGGT GTTTTACAAG TGAAATACAT TCCTATTTGG 1980
TAAACAGTTA CATTTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGGAGCTT GTCTGAGTTG GAATGCAGAG 2160
TTGCACTGCA AAATGTCAGG AAATGGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTCAACAA GGTAAGATGG TATCCTAGCA ACTGCGGATT 2340
TTAATACATT TCAGCAGAA GTACTTAGTT AATCTCTACC TTTAGGGATC GTTTCATCAT 2400
TTTTAGATGT TATACTTGAA ATACTGCATA ACTTTTAGCT TTCATGGGTT CCTTTTTTTC 2460
AGCCTTTAGG AGACTGTTAA GCAATTTGCT GTCCAACTTT TGTGTTGGTC TTAAACTGCA 2520
ATAGTAGTTT ACCTTGTATT GAAGAAATAA AGACCATTTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTGATGCT  2700
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
CCCGATTCCT TGAAAGGGCT CCAGCTTTAA TGCTTCCAAA TTGAAGGTGG CAGGCAACTT 3120
```

*FIG. 3a*

```
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GGCACTATTT TGGTTTGTAA 4140
AGCCTGTACT TCAAATATAT ATTTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TTGAGAAGAT GGCAGTTGCT 4500
TCTTTCCCTT TTTCCTGCTA AGTAAGGATT TTCCTGGC TTTGACACCT CACGAAATAG 4560
TCTTCCTGCC TTACATTCTG GCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACAGCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAATTC TTTCTTTTCC 5520
TGTCATGTGG GATCCCTACT GTGCCCTCCT GGTTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
AGTTCAGTCT CCTGCTGGGA CAGCTAACCG CATCTTATAA CCCCTTCTGA GACTCATCTT 6360
```

*FIG. 3b*

```
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CCAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGGACAAT CGCTTACCCC TCCCTGCTGG CTGCCCCTGT TTTGATGCAG 7140
CCCAGGGTAC TGTTGGCCTT TCAGGCTCCC AGACCCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTTATT ACTTCTATTA TGTACTTACT TTGACATAAC ACAGACACGC ACATATTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA AAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
GTATGAACTC AGGTCTCTCG GGCTACTGGC ATGGATTGAT TACATACAAC TGTAATTTTA 9600
```

*FIG. 3c*

```
GCAGTGATTT AGGGTTTATG AGTACTTTTG CAGTAAATCA TAGGGTTAGT AATGTTAATC  9660
TCAGGGAAAA AAAAAAAAAG CCAACCCTGA CAGACATCCC AGCTCAGGTG GAAATCAAGG  9720
ATCACAGCTC AGTGCGGTCC CAGAGAACAC AGGGACTCTT CTCTTAGGAC CTTTATGTAC  9780
AGGGCCTCAA GATAACTGAT GTTAGTCAGA AGACTTTCCA TTCTGGCCAC AGTTCAGCTG  9840
AGGCAATCCT GGAATTTTCT CTCCGCTGCA CAGTTCCAGT CATCCCAGTT TGTACAGTTC  9900
TGGCACTTTT TGGGTCAGGC CGTGATCCAA GGAGCAGAAG TTCCAGCTAT GGTCAGGGAG  9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTTCCCTGAC 10800
ATCCAATCTA AGCCTTCCCT CCTTGAGGTT AGATCCACTC CCCCTTGTGC TATCACTGTC 10860
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGGTGCGA TCTGCCTCAG ACCCACAGCC TGGGCAGCAG GAGGACCCTG ATGCTGCTGG 12000
CTCAGATGAG GAGAATCAGC CTGTTTAGCT GCCTGAAGGA TAGGCACGAT TTTGGCTTTC 12060
CTCAAGAGGA GTTTGGCAAC CAGTTTCAGA AGGCTGAGAC CATCCCTGTG CTGCACGAGA 12120
TGATCCAGCA GATCTTTAAC CTGTTTAGCA CCAAGGATAG CAGCGCTGCT TGGGATGAGA 12180
CCCTGCTGGA TAAGTTTTAC ACCGAGCTGT ACCAGCAGCT GAACGATCTG GAGGCTTGCG 12240
TGATCCAGGG CGTGGGCGTG ACCGAGACCC CTCTGATGAA GGAGGATAGC ATCCTGGCTG 12300
TGAGGAAGTA CTTTCAGAGG ATCACCCTGT ACCTGAAGGA GAAGAAGTAC AGCCCCTGCG 12360
CTTGGGAAGT CGTGAGGGCT GAGATCATGA GGAGCTTTAG CCTGAGCACC AACCTGCAAG 12420
AGAGCTTGAG GTCTAAGGAG TAAAAAGTCT AGAGTCGGGG CGGCCGGCCG CTTCGAGCAG 12480
ACATGATAAG ATACATTGAT GAGTTTGGAC AAACCACAAC TAGAATGCAG TGAAAAAAAT 12540
GCTTTATTTG TGAAATTTGT GATGCTATTG CTTTATTTGT AACCATTATA AGCTGCAATA 12600
AACAAGTTAA CAACAACAAT TGCATTCATT TTATGTTTCA GGTTCAGGGG GAGGTGTGGG 12660
AGGTTTTTTA AAGCAAGTAA AACCTCTACA AATGTGGTAA AATCGATAAG GATCCGTCGA 12720
GCGGCCGC                                                        12728
```

*FIG. 3d*

FIGURE 4: SEQ ID NO: 66

```
TGCGATCTGC CTCAGACCCA CAGCCTGGGC AGCAGGAGGA CCCTGATGCT GCTGGCTCAG    60
ATGAGGAGAA TCAGCCTGTT TAGCTGCCTG AAGGATAGGC ACGATTTTGG CTTTCCTCAA   120
GAGGAGTTTG CAACCAGTT TCAGAAGGCT GAGACCATCC CTGTGCTGCA CGAGATGATC   180
CAGCAGATCT TTAACCTGTT TAGCACCAAG GATAGCAGCG CTGCTTGGGA TGAGACCCTG   240
CTGGATAAGT TTTACACCGA GCTGTACCAG CAGCTGAACG ATCTGCAGGC TTGCGTGATC   300
CAGGGCGTGG GCGTGACCGA GACCCCTCTG ATGAAGGAGG ATAGCATCCT GCCTGTCAGG   360
AAGTACTTTC AGAGGATCAC CCTGTACCTG AAGGAGAAGA AGTACAGCCC CTGCGCTTGG   420
GAAGTCGTGA GGGCTGAGAT CATGAGGAGC TTTAGCCTGA GCACCAACCT GCAAGAGAGC   480
TTGAGGTCTA AGGAGTAA 498
```

SEQ ID NO: 67

```
TGCCGCCTTC TTTGATATTC ACTCTGTTGT ATTTCATCTC TTCTTGCCGA TGAAAGGATA    60
TAACAGTCTG TATAACAGTC TGTGAGGAAA TACTTGGTAT TTCTTCTGAT CAGTGTTTTT   120
ATAAGTAATG TTGAATATTG GATAAGGCTG TGTGTCCTTT GTCTTGGGAG ACAAAGCCCA   180
CAGCAGGTGG TGGTTGGGGT GGTGGCAGCT CAGTGACAGG AGAGGTTTTT TTGCCTGTTT   240
TTTTTTTTTT TTTTTTTTTT AAGTAAGGTG TTCTTTTTTC TTAGTAAATT TTCTACTGGA   300
CTGTATGTTT TGACAGGTCA GAAACATTTC TTCAAAAGAA GAACCTTTTG GAAACTGTAC   360
AGCCCTTTTC TTTCATTCCC TTTTTGCTTT CTGTGCCAAT GCCTTTGGTT CTGATTGCAT   420
TATGGAAAAC GTTGATCGGA ACTTGAGGTT TTATTTATA GTGTGGCTTG AAAGCTTGGA    480
TAGCTGTTGT TACACGAGAT ACCTTATTAA GTTAGGCCA GCTTGATGCT TTATTTTTC    540
CCTTTGAAGT AGTGAGCGTT CTCTGGTTTT TTTCCTTTGA AACTGGTGAG CTTAGATTT    600
TTCTAATGGG ATTTTTTACC TGATGATCTA GTTGCATACC CAAATGCTTG TAAATGTTTT   660
CCTAGTTAAC ATGTTGATAA CTTCGGATTT ACATGTTGTA TATACTTGTC ATCTGTGTTT   720
CTAGTAAAAA TATATGGCAT TTATAGAAAT ACGTAATTCC TGATTTCCTT TTTTTTATC    780
TCTATGCTCT GTGTGTACAG GTCAAACAGA CTTCACTCCT ATTTTATTT ATAGAATTTT    840
ATATGCAGTC TGTCGTTGGT TCTTGTGTTG TAAGGATACA GCCTTAAATT TCCTAGAGCG   900
ATGCTCAGTA AGGCGGGTTG TCACATGGGT TCAAATGTAA ACGGGCACG TTTGGCTGCT    960
GCCTTCCCGA GATCCAGGAC ACTAAACTGC TTCTGCACTG AGGTATAAAT CGCTTCAGAT  1020
CCCAGGGAAG TGCAGATCCA CGTGCATATT CTTAAAGAAG AATGAATACT TTCTAAAATA  1080
TTTTGGCATA GGAAGCAAGC TGCATGGATT TGTTTGGGAC TTAAATTATT TTGGTAACGG  1140
AGTGCATAGG TTTTAAACAC AGTTGCAGCA TGCTAACGAG TCACAGCGTT TATGCAGAAG  1200
TGATGCCTGG ATGCCTGTTG CAGCTGTTTA CGGCACTGCC TTGCAGTGAG CATTGCAGAT  1260
AGGGGTGGGG TGCTTTGTGT CGTGTTCCCA CACGCTGCCA CACAGCCACC TCCCGGAACA  1320
CATCTCACCT GCTGGGTACT TTTCAAACCA TCTTAGCAGT AGTAGATGAG TTACTATGAA  1380
ACAGAGAAGT TCCTCAGTTG GATATTCTCA TGGGATGTCT TTTTTCCCAT GTTGGGCAAA  1440
GTATGATAAA GCATCTCTAT TTGTAAATTA TGCACTTGTT AGTTCCTGAA TCCTTTCTAT  1500
AGCACCACTT ATTGCAGCAG GTGTAGGCTC TGGTGTGGCC TGTGTCTGTG CTTCAATCTT  1560
TTAAAGCTTC TTTGGAAATA CACTGACTTG ATTGAAGTCT CTTGAAGATA GTAAACAGTA  1620
CTTACCTTTG ATCCCAATGA AATCGAGCAT TTCAGTTGTA AAAGAATTCC GCCTATTCAT  1680
ACCATGTAAT GTAATTTTAC ACCCCAGTG CTGACACTTT GGAATATATT CAAGTAATAG   1740
ACTTTGGCCT CACCCTCTTG TGTACTGTAT TTTGTAATAG AAAATATTTT AAACTGTGCA  1800
TATGATTATT ACATTATGAA AGAGACATTC TGCTGATCTT CAAATGTAAG AAAATGAGGA  1860
GTGCGTGTGC TTTTATAAAT ACAAGTGATT GCAAATTAGT GCAGGTGTCC TTAAAAAAAA  1920
AAAAAAAAAG TAATATAAAA AGGACCAGGT GTTTTACAAG TGAAATACAT TCCTATTTGG  1980
TAAACAGTTA CATTTTTATG AAGATTACCA GCGCTGCTGA CTTTCTAAAC ATAAGGCTGT  2040
ATTGTCTTCC TGTACCATTG CATTTCCTCA TTCCCAATTT GCACAAGGAT GTCTGGGTAA  2100
ACTATTCAAG AAATGGCTTT GAAATACAGC ATGGGAGCTT GTCTGAGTTG GAATGCAGAG  2160
TTGCACTGCA AAATGTCAGG AAATGGATGT CTCTCAGAAT GCCCAACTCC AAAGGATTTT  2220
ATATGTGTAT ATAGTAAGCA GTTTCCTGAT TCCAGCAGGC CAAAGAGTCT GCTGAATGTT  2280
GTGTTGCCGG AGACCTGTAT TTCTCAACAA GGTAAGATGG TATCCTAGCA ACTGCGGATT  2340
TTAATACATT TTCAGCAGAA GTACTTAGTT AATCTCTACC TTTAGGGATC GTTTCATCAT  2400
TTTTAGATGT TATACTTGAA ATACTGCATA ACTTTTAGCT TTCATGGGTT CCTTTTTTC   2460
AGCCTTTAGG AGACTGTTAA GCAATTGCT GTCCAACTTT TGTGTTGGTC TTAAACTGCA   2520
ATAGTAGTTT ACCTTGTATT GAAGAAATAA AGACCATTTT TATATTAAAA AATACTTTG   2580
TCTGTCTTCA TTTTGACTTG TCTGATATCC TTGCAGTGCC CATTATGTCA GTTCTGTCAG  2640
ATATTCAGAC ATCAAAACTT AACGTGAGCT CAGTGGAGTT ACAGCTGCGG TTTTGATGCT  2700
GTTATTATTT CTGAAACTAG AAATGATGTT GTCTTCATCT GCTCATCAAA CACTTCATGC  2760
AGAGTGTAAG GCTAGTGAGA AATGCATACA TTATTGATA CTTTTTTAAA GTCAACTTTT   2820
TATCAGATTT TTTTTTCATT TGGAAATATA TTGTTTTCTA GACTGCATAG CTTCTGAATC  2880
TGAAATGCAG TCTGATTGGC ATGAAGAAGC ACAGCACTCT TCATCTTACT TAAACTTCAT  2940
TTTGGAATGA AGGAAGTTAA GCAAGGGCAC AGGTCCATGA AATAGAGACA GTGCGCTCAG  3000
GAGAAAGTGA ACCTGGATTT CTTTGGCTAG TGTTCTAAAT CTGTAGTGAG GAAAGTAACA  3060
```

*FIG. 5a*

```
CCCGATTCCT TGAAAGGGCT CCAGCTTTAA TGCTTCCAAA TTGAAGGTGG CAGGCAACTT 3120
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAATGGG TTTTAAAAAA GAAAACACAA 3900
AGGCAAAACC GGCTGCCCCA TGAAGAAGA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GGCACTATTT TGGTTTGTAA 4140
AGCCTGTACT TCAAATATAT ATTTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TTGAGAAGAT GGCAGTTGCT 4500
TCTTTCCCTT TTTCCTGCTA AGTAAGGATT TTCTCCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCCAC TGCAGGCTTA 4920
GAAAGTATGT GGCTCTGCCT GGGTGTGTTA CAGCTCTGCC CTGGTGAAAG GGGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAAATTC TTTCTTTTCC 5520
TGTCATGTGG GATCCCTACT GTGCCCTCCT GGTTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
```

FIG. 5b

```
AGTTCAGTCT CCTGCTGGGA CAGCTAACCG CATCTTATAA CCCCTTCTGA GACTCATCTT 6360
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CCAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGGACAAT CGCTTACCCC TCCCTGCTGG CTGCCCCTGT TTTGATGCAG 7140
CCCAGGGTAC TGTTGGCCTT TCAGGCTCCC AGACCCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTGTGTTTG 7680
CTTCAGCAGC CATTTAATTC TTCAGTGTCA TCTTGTTCTG TTGATGCCAC TGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA AAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAAAGAAAG TGCTCTTCTT 8760
TTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
```

*FIG. 5c*

```
GTATGAACTC AGGTCTCTCG GGCTACTGGC ATGGATTGAT TACATACAAC TGTAATTTTA 9600
GCAGTGATTT AGGGTTTATG AGTACTTTTG CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTTCCCTGAC 10800
ATCCAATCTA AGCCTTCCCT CCTTGAGGTT AGATCCACTC CCCCTTGTGC TATCACTGTC 10860
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCACCCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGG                                                       11945
```

FIG. 5d

FIGURE 6: SEQ ID NO: 68

```
AAAGTCTAGA GTCGGGGCGG CCGGCCGCTT CGAGCAGACA TGATAAGATA CATTGATGAG    60
TTTGGACAAA CCACAACTAG AATGCAGTGA AAAAAATGCT TTATTTGTGA AATTGTGAT   120
GCTATTGCTT TATTTGTAAC CATTATAAGC TGCAATAAAC AAGTTAACAA CAACAATTGC   180
ATTCATTTTA TGTTTCAGGT TCAGGGGGAG GTGTGGGAGG TTTTTTAAAG CAAGTAAAAC   240
CTCTACAAAT GTGGTAAAAT CGATAAGGAT CCGTCGAGCG GCCGC   285
```

AVIAN LYSOZYME PROMOTER

The present application claims the benefit of priority from a provisional application filed Mar. 30, 2001 and having U.S. Ser. No. 60/280,004.

FIELD OF THE INVENTION

The present invention relates generally to the identification of an avian lysozyme gene expression control region, specifically from the chicken. More specifically, the invention relates to recombinant nucleic acids and expression vectors, transfected cells and transgenic animals, especially chickens, that comprise the avian lysozyme gene expression control region operably linked to a polypeptide-encoding nucleic acid. The present invention further relates to the expression of the polypeptide-encoding nucleic acid under the control of the isolated avian lysozyme gene expression control region.

BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology to convert animals into "protein factories" for the production of specific proteins or other substances of pharmaceutical interest (Gordon et al., 1987, *Biotechnology* 5: 1183–1187; Wilmut et al., 1990, *Theriogenology* 33: 113–123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

Historically, transgenic animals have been produced almost exclusively by microinjection of the fertilized egg. The pronuclei of fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (e.g., Krimpenfort et al., in U.S. Pat. No. 5,175,384).

One system that holds potential is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct which is lined with tubular gland cells. These cells secrete the egg-white proteins, including ovalbumin, lysozyme, ovomucoid, conalbumin and ovomucin, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. As a result, efforts have been made to create transgenic chickens expressing heterologous proteins in the oviduct by means of microinjection of DNA (PCT Publication WO 97/47739).

The chicken lysozyme gene is highly expressed in the myeloid lineage of hematopoietic cells, and in the tubular glands of the mature hen oviduct (Hauser et al., 1981, *Hematol. and Blood Transfusion* 26: 175–178; Schutz et al., 1978, Cold Spring Harbor Symp. Quart. Biol. 42: 617–624) and is therefore a suitable candidate for an efficient promoter for heterologous protein production in transgenic animals. The regulatory region of the lysozyme locus extends over at least 12 kb of DNA 5' upstream of the transcription start site, and comprises a number of elements that have been individually isolated and characterized. The known elements include three enhancer sequences at about −6.1 kb, −3.9 kb, and −2.7 kb (Grewal et al., 1992, *Mol. Cell Biol.* 12: 2339–2350; Banifer et al., 1996, *J. Mol. Med.* 74: 663–671), a hormone responsive element (Hecht et al., 1988, *E.M.B.O.J.* 7: 2063–2073), a silencer element and a complex proximal promoter. The constituent elements of the lysozyme gene expression control region are identifiable as DNAase 1 hypersensitive chromatin sites (DHS). They may be differentially exposed to nuclease digestion depending upon the differentiation stage of the cell. For example, in the multipotent progenitor stage of myelomoncytic cell development, or in erythroblasts, the silencer element is a DHS. At the myeloblast stage, a transcription enchancer located −6.1 kb upstream from the gene transcription start site is a DHS, while at the later monocytic stage another enhancer, at −2.7 kb becomes DNAase sensitive (Huber et al., 1995, *DNA and Cell Biol.* 14: 397–402).

Scattered throughout the chicken genome, including the chicken lysozyme locus, are short stretches of nucleic acid that resemble features of Long Terminal Repeats (LTRs) of retrovirus. The function of these elements is unclear but most likely help define the DHS regions of a gene locus (Stein et al., 1983, *Proc. Natl. Acad. Sci. U.S.A.* 80: 6485–6489).

Flanking the lysozyme gene, including the regulatory region, are matrix attachment regions (5' MAR & 3' MAR), alternatively referred to as "scaffold attachment regions" or SARs. The outer boundaries of the chicken lysozyme locus have been defined by the MARs (Phi-Van et al., 1988, *E.M.B.O.J.* 7: 655–664; Phi-Van, L. and Stratling, W. H., 1996, *Biochem.* 35: 10735–10742). Deletion of a 1.32 kb or a 1.45 kb halves region, each comprising half of a 5' MAR, reduces positional variation in the level of transgene expression (Phi-Van and Stratling, supra).

The 5' matrix-associated region (5' MAR), located about −11.7 kb upstream of the chicken lysozyme transcription start site, can increase the level of gene expression by limiting the positional effects exerted against a transgene (Phi-Van et al., 1988, supra). At least one other MAR is located 3' downstream of the protein encoding region. Although MAR nucleic acid sequences are conserved, little cross-hybridization is seen, indicating significant overall sequence variation. However, MARs of different species can interact with the nucleomatrices of heterologous species, to the extent that the chicken lysozyme MAR can associate with the plant tobacco nucleomatrix as well as that of the chicken oviduct cells (Mlynarona et al., 1994, *Cell* 6: 417–426; von Kries et al., 1990, *Nucleic Acids Res.* 18: 3881–3885).

Gene expression must be considered not only from the perspective of cis-regulatory elements associated with a gene, and their interactions with transacting elements, but also with regard to the genetic environment in which they are located. Chromosomal positioning effects (CPEs), therefore, are the variations in levels of transgene expression associated with different locations of the transgene within the recipient genome. An important factor governing CPE upon the level of transgene expression is the chromatin structure around a transgene, and how it cooperates with the cis-regulatory elements. The cis-elements of the lysozyme locus are confined within a single chromatin domain (Banifer et al., 1996, supra; Sippel et al., pgs. 133–147 in Eckstein F. & Lilley D. M. J. (eds), "Nucleic Acids and Molecular Biology", Vol. 3, 1989, Springer.

Deletion of a cis-regulatory element from a transgenic lysozyme locus is sufficient to reduce or eliminate positional independence of the level of gene expression (Banifer et al., 1996, supra). There is also evidence indicating that positional independence conferred on a transgene requires the cotransfer of many kilobases of DNA other than just the protein encoding region and the immediate cis-regulatory elements.

The lysozyme promoter region of chicken is active when transfected into mouse fibroblast cells and linked to a reporter gene such as the bacterial chloramphenicol acetyltransferase (CAT) gene. The promoter element is also effective when transiently transfected into chicken promacrophage cells. In each case, however, the presence of a 5' MAR element increased positional independency of the level of transcription (Stief et al., 1989, Nature 341: 343–345; Sippel et al., pgs. 257–265 in Houdeline L. M. (ed), "Transgenic Animals: Generation and Use").

The ability to direct the insertion of a transgene into a site in the genome of an animal where the positional effect is limited offers predictability of results during the development of a desired transgenic animal, and increased yields of the expressed product. Sippel and Steif disclose, in U.S. Pat. No. 5,731,178, methods to increase the expression of genes introduced into eukaryotic cells by flanking a transcription unit with scaffold attachment elements, in particular the 5' MAR isolated from the chicken lysozyme gene. The transcription unit disclosed by Sippel and Steif was an artificial construct that combined only the −6.1 kb enhancer element and the proximal promoter element (base position −579 to +15) from the lysozyme gene. Other promoter associated elements were not included. However, although individual cis-regulatory elements have been isolated and sequenced, together with short regions flanking DNA, the entire nucleic acid sequence comprising the functional 5' upstream region of the lysozyme gene has not been determined in its entirety and therefore not employed as a functional promoter to allow expression of a heterologous transgene.

What is still needed, however, is an efficient transcription promoter that will allow expression of a transgene in avian cells that is not subject to positional variation.

What is also needed is a gene expression promoter cassette that will allow expression of a transgene in the oviduct cells of an avian and efficient gene expression regardless of the chromosomal location of the expression system.

SUMMARY OF THE INVENTION

Briefly described, the present invention relates to a novel isolated avian nucleic acid comprising an avian lysozyme gene expression control region.

The isolated nucleic acid of the present invention is useful for reducing the chromosomal positional effect of a transgene operably linked to the lysozyme gene expression control region and transfected into a recipient cell. By isolating a region of the avian genome extending from 5' upstream of a 5' MAR of the lysozyme locus to the junction between the signal peptide sequence and a polypeptide-encoding region, cis-elements are also included to allow gene expression in a tissue-specific manner. The lysozyme promoter region of the present invention, therefore, will allow expression of an operably linked heterologous nucleic acid insert in a transfected avian cell such as, for example, an oviduct cell.

One aspect of the present invention provides a novel isolated nucleic acid that is located immediately 5' upstream of the native lysozyme-encoding region of the chicken lysozyme gene locus. The novel isolated avian nucleic acid sequence encoding a lysozyme gene expression control region comprises at least one 5' matrix attachment region, an intrinsically curved DNA region, at least one transcription enhancer element, a negative regulatory element, at least one hormone responsive element, at least one avian CR1 repeat element, and a proximal lysozyme promoter and signal peptide-encoding region. Interspersed between these constituent elements are stretches of nucleic acid that serve at least to organize the above elements in an ordered array relative to a polypeptide-encoding region.

In one embodiment of the present invention the isolated nucleic acid is isolated from a chicken.

The isolated avian lysozyme of the present invention may be operably linked with a selected nucleic acid insert, wherein the nucleic acid insert encodes a polypeptide desired to be expressed in a transfected cell. The nucleic acid insert may be placed in frame with a signal peptide sequence. Translation initiation may start with the signal peptide and continue through the nucleic acid insert, thereby producing an expressed polypeptide having the desired amino acid sequence.

The recombinant DNA of the present invention may further comprise a polyadenylation signal sequence that will allow the transcript directed by the novel lysozyme gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like.

The sequence of the expressed nucleic acid insert may be optimized for codon usage by a host cell. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken.

Yet another aspect of the present invention are expression vectors suitable for delivery to a recipient cell for expression of the vector therein. The expression vector of the present invention may comprise an isolated avian lysozyme gene expression control region operably linked to a nucleic acid insert encoding a polypeptide, and optionally a polyadenylation signal sequence. The expression vector may further comprise a bacterial plasmid sequence, a viral nucleic acid sequence, or fragments or variants thereof that may allow for replication of the vector in a suitable host.

Another aspect of the present invention is a method of expressing a heterologous polypeptide in a eukaryotic cell by transfecting the cell with a recombinant DNA comprising an avian lysozyme gene expression control region operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

Also within the scope of the present invention are recombinant cells, tissues and animals containing non-naturally occurring recombinant nucleic acid molecules according to the present invention and described above. In one embodiment of the present invention, the transformed cell is a chicken oviduct cell and the nucleic acid insert comprises the chicken lysozyme gene expression control region, a nucleic acid insert encoding a human interferon α2b and codon optimized for expression in an avian cell, and an SV40 polyadenylation sequence.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 1a. FIG. 1b. FIG. 1c, and Fig. 1d illustrate the primers (SEQ ID NOS: 1–64) used in the sequencing of the lysozyme gene expression control region (SEQ ID NO: 67).

FIG. 3a, FIG. 3b, FIG. 3c and FIG. 3d illustrate the nucleic acid sequence (SEQ ID NO: 65) comprising the chicken lysozyme gene expression control region (SEQ ID NO: 67), the nucleic acid sequence SEQ ID NO: 66 encoding the chicken expression optimized human interferon α2b (IFNMAGMAX) which is underlined in the figures and the SV40 polyadenylation signal sequence (SEQ ID NO: 68) which is in bold print in the figures.

FIG. 4 illustrates the nucleic acid sequence SEQ ID NO: 66 encoding the chicken expression optimized human interferon α2b (IFNMAGMAX).

FIGS. 5a, 5b, 5c and 5d illustrate the nucleic acid sequence SEQ ID NO: 67 encoding the chicken lysozyme gene expression control region.

FIG. 6 illustrates the nucleic acid sequence SEQ ID NO: 68 encoding the 5V40 polyadenylation signal sequence.

DETAILED DESCRIPTION OF THE PREFERRED EMBODIMENTS

Figure 2:
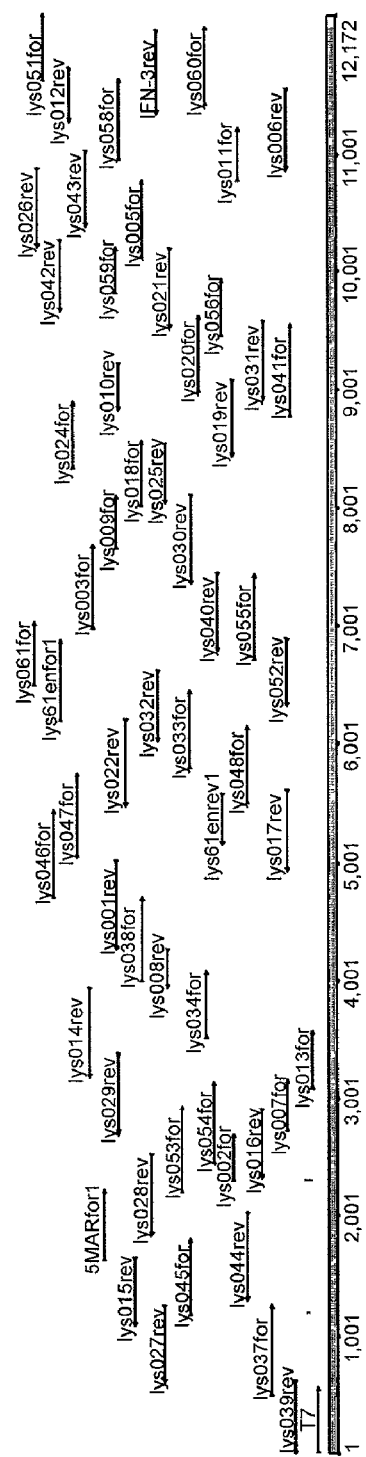
FIG. 2 schematically illustrates the approximately 12 kb lysozyme gene expression control region (SEQ ID NO: 67), indicating the relative positions and orientations of the primers (SEQ ID NOS: 1–64) used in the sequencing thereof.

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

This description uses gene nomenclature accepted by the Cucurbit Genetics Cooperative as it appears in the *Cucurbit Genetics Cooperative Report* 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

For convenience, certain terms employed in the specification, examples, and appended claims are collected here.

Definitions

The term "animal" is used herein to include all vertebrate animals, including avians and humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes a lysozyme gene expression control region or a variant thereof of the present invention.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term "significant" as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or noncovalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation from an RNA polymerase. A "promoter-proximal element" may be a regulatory sequence within about 200 base pairs of the transcription start site.

The terms "matrix attachment regions" or "SAR elements" as used herein refer to DNA sequences having an affinity or intrinsic binding ability for the nuclear scaffold or matrix. The MAR elements of the chicken lysozyme locus were described by Phi-Van et al., 1988, E.M.B.O. J. 76: 665–664 and Phi-Van, L. and Stratling, W. H., 1996, Biochem. 35: 10735–10742, the contents of which are incorporated herein by reference in their entireties.

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a lysozyme gene expression control region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g., low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° C. in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al., 1984, Anal. Biochem. 138: 267–284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al., 1989, "Molecular Cloning: A Laboratory Manual", 2nd ed., Cold Spring Harbor Press, the contents of which are herein incorporated by reference in its entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of Karlin and Attschul, 1990, *Proc. Natl. Acad. Sci.* 87: 2264–2268, modified as in Karlin and Attschul, 1993, *Proc. Natl. Acad. Sci.* 90: 5873–5877. Such an algorithm is incorporated into the NBLAST and XBLAST programs of Attschul et al., 1990, *T. Mol. Biol.* Q15: 403–410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al., 1997, *Nucl. Acids Res.* 25: 3389–3402. When utilizing BLAST and Gapped BLAST programs, the default parameters of the respective programs (e.g. XBLAST and NBLAST) are used. See http://www.ncbi.nlm.nih.gov. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises the lysozyme gene expression control region operably linked to a nucleotide sequence coding at least one polypeptide. As used herein, the term "regulatory sequences" includes promoters, enhancers, and other elements that may control gene expression. Standard molecular biology textbooks such as Sambrook et al. eds., 1989, "Molecular Cloning: A Laboratory Manual", 2nd ed., Cold Spring Harbor Press may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell, preferably an avian cell, and more preferably a chicken male germ cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to the male germ cells using specific ligands that are recognized by receptors on the cell surface of the germ cell, such as the c-kit ligand or modifications thereof.

Other preferred transfecting agents include but are not limited to LIPOFECTAMINE™ (i.e.. DOSPA N-[)2-({2,5-bis[3-aminopropyl)amino]-1-oxypentyl}amino)ethyl]-N.N-dimethyl-1-2,3-bis(9-octadecenyloxy)-1 -propanaminium trifluoroacetate), DIMRIE C™, SUPERFECT®, and EFFECTENE™, (Qiagen), UNIFECTIN™, MAXIFECTIN™, LIPOFECTIN® (i.e., DOTMA (N-[1-(2.3-dioleyloxy)propyl]-N,N,N-trimethylammonium chloride)), DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N -dihydroxyethyl ammonium bromide), HDEAB (N-n-hexadecylN,N -dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

Pharmaceutical compositions comprising agents that will modulate the regulation of the expression of a polypeptide-encoding nucleic acid operably linked to a lysozyme gene expression control region can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Pharmaceutical compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Pharmaceutical compositions may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Science", 17th edition, 1985 may be consulted to prepare suitable preparations, without undue experimentation. Dosages can generally range from a few hundred milligrams to a few grams.

As used herein, a "transgenic animal" is any animal, such as an avian species, including the chicken, in which one or more of the cells of the avian may contain heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject polypeptide, e.g., either agonistic or antagonistic forms, or in which the gene has been disrupted. The terms "chimeric animal" or "mosaic animal" are used herein to refer to animals in which the recombinant gene is found, or in which the recombinant is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene according to the present invention will include one or more transcriptional regulatory sequences, polyadenylation signal sequences and any other nucleic acid, such as introns, that may be necessary for optimal expression of a selected nucleic acid.

The term "chromosomal positional effect (CPE)" as used herein refers to the variation in the degree of gene transcription as a function of the location of the transcribed locus within the cell genome. Random transgenesis may result in a transgene being inserted at different locations in the genome so that individual cells of a population of transgenic cells may each have at least one transgene, each at a different location and therefore each in a different genetic environment. Each cell, therefore, may express the transgene at a level specific for that particular cell and dependent upon the immediate genetic environment of the transgene. In a transgenic animal, as a consequence, different tissues may exhibit different levels of transgene expression.

Techniques useful for isolating and characterizing the nucleic acids and proteins of the present invention are well known to those of skill in the art and standard molecular biology and biochemical manuals may be consulted to select suitable protocols without undue experimentation. See, for example, Sambrook et al, 1989, "Molecular Cloning: A Laboratory Manual", 2nd ed., Cold Spring Harbor, the content of which is herein incorporated by reference in its entirety.

Abbreviations:

Abbreviations used in the present specification include the following: aa, amino acid(s); bp, base pair(s); cDNA, DNA complementary to RNA; nt, nucleotide(s); SSC, sodium chloride-sodium citrate; DMSO, dimethyl sulfoxide; MAR; matrix attachment region.

Chicken lysozyme gene expression control region nucleic acid sequences: A series of PCR amplifications of template chicken genomic DNA were used to isolate the gene expression control region of the chicken lysozyme locus. Two amplification reactions used the PCR primer sets SEQ ID NOS: 1 and 2 and SEQ ID NOS: 3 and 4. The amplified PCR products were united as a contiguous isolated nucleic acid by a third PCR amplification step with the primers SEQ ID NOS: 1 and 4, as described in Example 1 below.

The isolated PCR-amplified product, comprising about 12 kb of the nucleic acid region 5' upstream of the native chicken lysozyme gene locus, was cloned into the plasmid pCMV-LysSPIFNMM. pCMV-LysSPIFNMM comprises a modified nucleic acid insert encoding a human interferon α2b sequence and an SV40 polyadenylation signal sequence 3' downstream of the interferon encoding nucleic acid. The sequence SEQ ID NO: 66 of the nucleic acid insert encoding human interferon α2b was in accordance with avian cell codon usage, as determined from the nucleotide sequences encoding chicken ovomucin, ovalbumin, ovotransferrin and lysozyme. The novel chicken lysozyme gene expression control region, interferon-encoding insert and the SV40 polyadenylation signal sequence of the resulting plasmid construct pAVIJCR-A115.93.1.2, constructed as described in Example 1 below, was sequenced using the artificial oligonucleotide primers SEQ ID NOS: 1–64, as illustrated in FIGS. 1 and 2.

The nucleic acid sequence (SEQ ID NO: 65) (GenBank Accession No. AF405538) of the insert in pAVIJCR-A115.93.1.2 is shown in FIG. 3, with the modified human interferon α2b encoding nucleotide sequence SEQ ID NO: 66 (GenBank Accession No. AF405539) and the novel chicken lysozyme gene expression control region SEQ ID NO: 67 (GenBank Accession No. AF405540) shown in FIGS. 4 and 5 respectively. A polyadenylation signal sequence that is suitable for operably linking to the polypeptide-encoding nucleic acid insert is the SV40 signal sequence SEQ ID NO: 68, as shown in FIG. 6.

The inclusion of the novel isolated avian lysozyme gene expression control region of the present invention upstream of a codon-optimized interferon-encoding sequence in pAVIJCR-A115.93.1.2 allowed expression of the interferon polypeptide in transfected avian cells, as described in Example 5, below. It is contemplated, however, that any nucleic acid sequence encoding a polypeptide may be operably linked to the novel isolated avian lysozyme gene expression control region so as to be expressed in a transfected avian cell. The plasmid construct pAVIJCR-A115.93.1.2 was transfected into cultured quail oviduct cells, which were then incubated for about 72 hours. ELISA assays of the cultured media showed that the transfected cells synthesized a polypeptide detectable with anti-human interferon α2b antibodies.

The novel isolated chicken lysozyme gene expression control region of the present invention comprises the nucleotide elements that are positioned 5' upstream of the lysozyme-encoding region of the native chicken lysozyme locus and which are necessary for the regulated expression of a downstream polypeptide-encoding nucleic acid. While not wishing to be bound by any one theory, the inclusion of at least one 5' MAR element in the isolated control region may confer positional independence to a transfected gene operably linked to the novel lysozyme gene expression control region.

The isolated lysozyme gene expression control region of the present invention is useful for reducing the chromosomal positional effect of a transgene operably linked to the lysozyme gene expression control region and transfected into a recipient avian cell. By isolating a region of the avian genome extending from a point 5' upstream of a 5' MAR of the lysozyme locus to the junction between the signal peptide sequence and a polypeptide-encoding region, cis-regulatory elements are also included that may allow gene expression in a tissue-specific manner. The lysozyme promoter region of the present invention, therefore, will allow expression of an operably linked heterologous nucleic acid insert in a transfected avian cell such as, for example, an oviduct cell.

One aspect of the present invention, therefore, provides a novel isolated nucleic acid that comprises the nucleotide sequence SEQ ID NO: 67, shown in FIG. 5 (Genbank Accession No. AF405540) and derivatives and variants thereof, that is located immediately 5' upstream of the native lysozyme-encoding region of the chicken lysozyme gene locus.

In one embodiment of the novel isolated nucleic acid of the present invention, therefore, the avian nucleic acid sequence encoding a lysozyme gene expression control region comprises at least one 5' matrix attachment region, an intrinsically curved DNA region, at least one transcription enhancer element, a negative regulatory element, at least one hormone responsive element, at least one avian CR1 repeat element, and a proximal lysozyme promoter and signal peptide-encoding region. Interspersed between these constituent elements are stretches of nucleic acid that serve at least to organize the above elements in an ordered array relative to a polypeptide-encoding region, such as that encoding for chicken lysozyme. It is contemplated to be within the scope of the present invention that the cis-elements of the lysozyme gene expression control region may be in any linear arrangement that can allow the formation of a transcript comprising the nucleotide sequence or its complement of a nucleic insert operably linked to the lysozyme gene expression control region.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 67, as shown in FIG. 5, or a variant thereof.

Another aspect of the invention provides nucleic acids that can hybridize under high, medium or low stringency conditions to an isolated nucleic acid that encodes a chicken lysozyme gene expression control region having all, a derivative of, or a portion of the nucleic acid sequence SEQ ID NO: 67 shown in FIG. 5. The nucleotide sequence determined from the isolation of the lysozyme gene expression control region from a chicken (SEQ ID NO: 67) will allow for the generation of probes designed for use in identifying homologs of lysozyme gene expression control regions in other avian species.

Fragments of a nucleic acid encoding a portion of the subject lysozyme gene expression control region are also within the scope of the invention. As used herein, a fragment of the nucleic acid encoding an active portion of a lysozyme gene expression control region refers to a nucleotide sequence having fewer nucleotides than the nucleotide sequence encoding the entire nucleic acid sequence of the lysozyme gene expression control region.

In one embodiment of the present invention, the nucleotide sequence of the isolated DNA molecule of the present invention may be used as a probe in nucleic acid hybridization assays for the detection of the lysozyme gene expression control region. The nucleotide sequence of the present invention may be used in any nucleic acid hybridization assay system known in the art, including, but not limited to, Southern blots (Southern, E. M., 1975, *J. Mol. Biol.* 98: 508), Northern blots (Thomas et al., 1980, *Proc. Natl. Acad. Sci.* 77: 5201–05), and Colony blots (Grunstein et al., 1975, *Proc. Natl. Acad. Sci.* 72: 3961–65)(the contents of which are hereby incorporated by reference in their entireties). Alternatively, the isolated DNA molecules of the present invention can be used in a gene amplification detection procedure such as a polymerase chain reaction (Erlich et al., 1991, *Science* 252: 1643–51, the content of which is hereby incorporated by reference in its entirety) or in restriction fragment length polymorphism (RFLP) diagnostic techniques, as described in pgs. 519–522 and 545–547 of Watson et al., 2nd ed., 1992, "Recombinant DNA", Scientific American Books (the contents of which is hereby incorporated by reference in its entirety).

Nucleotides constructed in accordance with the present invention can be labeled to provide a signal as a means of detection. For example, radioactive elements such as $^{32}P$, $^{3}H$, and $^{35}S$ or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals, such as *Promega: Protocol and Applications Guide,* 2nd Edition, 1991 (Promega Corp., Madison, Wis., the content of which is incorporated herein in its entirety), may be consulted to select an appropriate labeling protocol without undue experimentation.

In another embodiment of the present invention, an isolated nucleic acid molecule of the present invention includes a nucleic acid that is at least about 75%, preferably at least about 80%, more preferably at least about 85%, even more preferably at least about 90%, still more preferably at least about 95%, and even more preferably at least about 99%, identical to a chicken-derived lysozyme gene expression control region-encoding nucleic acid molecule as depicted in SEQ ID NO: 67.

In another embodiment of the present invention, an avian lysozyme gene expression control region gene or nucleic acid molecule can be an allelic variant of SEQ ID NO: 67.

The present invention also contemplates the use of anti-sense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

The nucleic acid sequence of a chicken lysozyme gene expression control region nucleic acid molecule (SEQ ID NO: 67) of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain lysozyme gene expression control region nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian lysozyme gene expression control region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of preferred libraries to screen, or from which to amplify nucleic acid molecules, include but are not limited to mammalian BAC libraries, genomic DNA libraries, and cDNA libraries. Similarly, preferred sequence databases useful for screening to identify sequences in other species homologous to chicken lysozyme gene expression control region include, but are not limited to, GenBank and the mammalian Gene Index database of The Institute of Genomics Research (TIGR).

Codon-optimized Proteins

Another aspect of the present invention is a recombinant DNA molecule comprising the novel isolated avian lysozyme gene expression control region of the present invention operably linked to a selected polypeptide-encoding nucleic acid insert, and which may express the nucleic acid insert when transfected to a suitable host cell, preferably an avian cell. The nucleic acid insert may be placed in frame with a signal peptide sequence, whereby translation initiation from the transcript may start with the signal peptide and continue through the nucleic acid insert, thereby producing an expressed polypeptide having the desired amino acid sequence.

It is anticipated that the recombinant DNA, therefore, may further comprise a polyadenylation signal sequence that will allow the transcript directed by the novel lysozyme gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like, or derivatives thereof.

In one embodiment of the recombinant DNA of the present invention, the polyadenylation signal sequence is derived from the SV40 virus.

In another embodiment of the recombinant DNA of the present invention, the polyadenylation signal has the nucleic acid sequence SEQ ID NO: 68 or a variant thereof, as shown in FIG. 6.

Another aspect of the present invention is to provide nucleic acid sequences of a human interferon α2b protein optimized for expression in avian cells, and derivatives and fragments thereof.

In derivatives of the human interferon α2b protein of the present invention, for example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, "Biochemistry", 2nd ed, L. Stryer, ed., WH Freeman and Co.,1981). Peptides in which more than one replacement has taken place can readily be tested in the same manner.

One embodiment of the present invention is a recombinant DNA molecule comprising the isolated avian lysozyme gene expression control region of the present invention, operably linked to a nucleic acid insert encoding a polypeptide, and a polyadenylation signal sequence optionally operably linked thereto. It is contemplated that when the recombinant DNA is to be delivered to a recipient cell for expression therein, the sequence of the nucleic acid sequence may be modified so that the codons are optimized for the codon usage of the recipient species. For example, if the recombinant DNA is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken.

In one embodiment of the recombinant DNA of the present invention, therefore, the nucleic acid insert encodes the human interferon α2b polypeptide. Optimization of the sequence for codon usage elevates the level of translation in avian eggs. In this embodiment, the sequence (SEQ ID NO: 66) of the optimized human interferon sequence is shown in FIG. 4.

In yet another embodiment of the present invention, the recombinant DNA comprises the isolated avian lysozyme gene expression control region operably linked to a nucleic acid encoding a human interferon α2b and the SV40 polyadenylation sequence, the recombinant DNA having the nucleotide sequence SEQ ID NO: 65, as shown in FIG. 3, or a variant thereof.

The protein of the present invention may be produced in purified form by any known conventional techniques. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

Recombinant Nucleic Acids, and Expression Thereof, Under the Control of an Avian Lysozyme Promoter:

Another potentially useful application of the novel isolated lysozyme gene expression control region of the present invention is the possibility of increasing the amount of a heterologous protein present in a bird, (especially the chicken) by gene transfer. In most instances, a heterologous polypeptide-encoding nucleic acid insert transferred into the recipient animal host will operably linked with the lysozyme gene expression control region, to allow the cell to initiate and continue production of the genetic product protein. A recombinant DNA molecule of the present invention can be transferred into the extra-chromosomal or genomic DNA of the host.

The recombinant DNA nucleic acid molecules of the present invention can be delivered to cells using conventional recombinant DNA technology. The recombinant DNA molecule may be inserted into a cell to which the recombinant DNA molecule is heterologous (i.e. not normally present). Alternatively, as described more fully below, the recombinant DNA molecule may be introduced into cells which normally contain the recombinant DNA molecule, for example, to correct a deficiency in the expression of a polypeptide, or where over-expression of the polypeptide is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated lysozyme gene expression control region.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an expression vector suitable for delivery to a recipient cell for expression of the vector therein. It is contemplated to be within the scope of the present invention for the expression vector to comprise an isolated avian lysozyme gene expression control region operably linked to a nucleic acid insert encoding a polypeptide, and optionally a polyadenylation signal sequence. The expression vector of the present invention may further comprise a bacterial plasmid sequence, a viral nucleic acid sequence, or fragments or variants thereof that may allow for replication of the vector in a suitable host.

The novel isolated avian lysozyme gene expression control region of the present invention (SEQ ID NO: 67) and a polypeptide-encoding nucleic acid sequence operably linked thereto, such as, for example, SEQ ID NO: 66 or a derivative or truncated variant thereof, and optionally a polyadenylation signal sequence such as, for example, SEQ ID NO: 68, may be introduced into viruses such as vaccinia virus. Methods for making a viral recombinant vector useful for expressing a protein under the control of the lysozyme promoter are analogous to the methods disclosed in U.S. Pat. Nos. 4,603,112; 4,769,330; 5,174,993; 5,505,941; 5,338,683; 5,494,807; 4,722,848; Paoletti, E., 1996, *Proc. Natl. Acad. Sci.*, 93: 11349–11353; Moss, B., 1996, *Proc. Natl. Acad. Sci.* 93: 11341–11348; Roizman, 1996, *Proc. Natl. Acad. Sci.* 93: 11307–11302; Frolov et al., 1996, *Proc. Natl. Acad. Sci.* 93: 11371–11377; Grunhaus et al., 1993, *Seminars in Virology* 3: 237–252 and U.S. Pat. Nos. 5,591,639; 5,589,466; and 5,580,859 relating to DNA expression vectors, inter alia; the contents of which are incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier, F. W. et. al., 1990, *Use of T7 RNA Polymerase to Direct Expression of Cloned Genes* in "Gene Expression Technology," vol. 185, which is hereby incorporated by reference in its entirety) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., 1982, *Molecular Cloning: A Laboratory Manual*, Cold Springs Laboratory, Cold Springs Harbor, N.Y., which is hereby incorporated by reference in its entirety.

A variety of host-vector systems may be utilized to express the protein-encoding sequence(s). Primarily, the vector system must be compatible with the host cell used. The use of eukaryotic recipient host cells permits partial or complete post-translational modification such as, but not only, glycosylation and/or the formation of the relevant inter- or intra-chain disulfide bonds. Host-vector systems include but are not limited to the following: bacteria transformed with bacteriophage DNA, plasmid DNA, or cosmid DNA; microorganisms such as yeast containing yeast vectors; vertebrate cell systems infected with virus (e.g., vaccinia virus, adenovirus, etc.); insect cell systems infected with virus (e.g., baculovirus) or avian embryonic cells inoculated with the recombinant nucleic acid. The expression elements of these vectors vary in their strength and specificities. Depending upon the host-vector system utilized, any one of a number of suitable transcription and translation elements can be used.

Once the novel isolated lysozyme gene expression control region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection and the like.

Another aspect of the present invention, therefore, is a method of expressing a heterologous polypeptide in a eukaryotic cell by transfecting the cell with a recombinant DNA comprising an avian lysozyme gene expression control region operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken lysozyme gene expression control region, a nucleic acid insert encoding a human interferon α2b and codon optimized for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal producing a heterologous protein expressed from a transfected nucleic acid according to the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian lysozyme gene expression control region according to the present invention is produced in the white of an egg.

Viral Vector Cell Transformation:

An exemplary approach for the in vivo introduction of a nucleic acid encoding the subject novel isolated lysozyme gene expression control region into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo. These vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid encoding a lysozyme gene expression control region, thereby rendering the retrovirus replication defective. Protocols for producing recombinant retroviruses and for infecting cells in vitro or in vivo with such viruses can be found in Ausubel et al, 1989, "Current Protocols in Molecular Biology," Sections 9.10–9.14, Greene Publishing Associates, and other standard laboratory manuals. Examples of suitable retroviruses include pLJ, pZIP, pWE and pEM, all of which are well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., 1989, *Proc. Natl. Acad. Sci.* 86: 9079–9083; Julan et al., 1992, *J. Gen. Virol.* 73: 3251–3255 and Goud et al., 1983, *Virology* 163: 251–254) or coupling cell surface ligands to the viral env proteins (Neda et al., 1991, *J. Biol. Chem.* 266: 14143–14146)(all of which are incorporated herein by reference in their entireties). Coupling can be in the form of the chemical cross-linking with a protein or other moiety (e.g., lactose to convert the env protein to an asialoglycoprotein), as well as by generating fusion proteins (e.g., single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., 1988, *Bio Techniques* 6: 616; Rosenfeld et al., 1991, *Science* 252: 43 1434; and Rosenfeld et al., 1992, *Cell* 68: 143–155, all of which are incorporated herein by reference in their entireties). Suitable adenoviral vectors derived from the adenovirus strain Ad type 5 d1324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., 1979, *Cell* 16:683; Berkner et al., supra; and Graham et al., 1991, pp. 109–127 in "Methods in Molecular Biology," vol. 7, E. J. Murray, ed., Humana, Clifton, N. J., all of which are incorporated herein by reference in their entireties). Expression of an inserted gene such as, for example, encoding the human interferon α2b, can be under control of the exogenously added lysozyme gene expression control region sequences.

Yet another viral vector system useful for delivery of, for example, the subject avian lysozyme gene expression control region operably linked to a nucleic acid encoding a polypeptide, is the adeno-associated virus (AAV). Vectors containing as little as 300 base pairs of AAV can be packaged and can integrate. Space for exogenous DNA is limited to about 4.5 kb. An AAV vector, such as that described in Tratschin et al., 1985, *Mol. Cell. Biol.* 5: 3251–3260, can be used to introduce DNA into cells. A variety of nucleic acids have been introduced into different cell types using AAV vectors (see, for example, Hermonat et al., 1984, *Proc. Natl. Acad. Sci.* 81: 6466–6470; Tratschin et al., 1985, *Mol. Cell. Biol.* 4: 2072–2081; Wondisford et al., 1988, *Mol. Endocrinol.* 2: 32–39; Tratschin et al., 1984, *J. Virol.* 51: 611–619; and Flotte et al., 1993, *J. Biol. Chem.* 268: 3781–3790, all of which are incorporated herein by reference in their entireties).

Non-viral Expression Vectors:

Most non-viral methods of gene transfer rely on normal mechanisms used by eukaryotic cells for the uptake and intracellular transport of macromolecules. In preferred embodiments, non-viral gene delivery systems of the present invention rely on endocytic pathways for the uptake of the subject lysozyme gene expression control region and operably linked polypeptide-encoding nucleic acid by the targeted cell. Exemplary gene delivery systems of this type include liposomal derived systems, poly-lysine conjugates, and artificial viral envelopes.

In a representative embodiment, a nucleic acid comprising the novel isolated lysozyme gene expression control region of the present invention can be entrapped in liposomes bearing positive charges on their surface (e.g., lipofectins) and (optionally) which are tagged with antibodies against cell surface antigens of the target tissue (Mizuno et al., 1992, *NO Shinkei Geka* 20: 547–551; PCT publication WO91/06309; Japanese patent application 1047381; and European patent publication EP-A-43075, all of which are incorporated herein by reference in their entireties).

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180, all of which are incorporated herein by reference in their entireties). It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., 1993, *Science* 260–926; Wagner et al., 1992, *Proc. Natl. Acad. Sci.* 89: 7934; and Christiano et al., 1993, *Proc. Natl. Acad. Sci.* 90: 2122, all of which are incorporated herein by reference in their entireties). It is further contemplated that a recombinant DNA molecule comprising the novel isolated lysozyme gene expression control region of the present invention may be delivered to a recipient host cell by other non-viral methods including by gene gun, microinjection, sperm-mediated transfer, or the like.

Transgenic Animals:

Another aspect of the present invention concerns transgenic animals, such as chickens, having a transgene comprising the novel isolated lysozyme gene expression control region of the present invention and which preferably (though optionally) express a heterologous gene in one or more cells in the animal. Suitable methods for the generation of transgenic avians having heterologous DNA incorporated therein are described, for example, in WO 99/19472 to Ivarie et al.; WO 00/11151 to Ivarie et al..; and WO 00/56932 to Harvey et al., all of which are incorporated herein by reference in their entirety.

In various embodiments of the present invention, the expression of the transgene may be restricted to specific subsets of cells, tissues or developmental stages utilizing, for example, cis-acting sequences acting on the lysozyme gene expression control region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences. The inclusion of a 5' MAR region in the novel isolated lysozyme gene expression control region of the present invention may allow the heterologous expression unit to escape the chromosomal positional effect (CPE) and therefore be expressed at a more uniform level in transgenic tissues that received the transgene by a route other than through germ line cells.

One embodiment of the present invention, therefore, is a transgenic avian having a heterologous polynucleotide sequence comprising a nucleic acid insert encoding the heterologous polypeptide and operably linked to the novel isolated avian lysozyme gene expression control region, the lysozyme gene expression control region comprising at least one 5' matrix attachment region, an intrinsically curved DNA region, at least one transcription enhancer, a negative regulatory element, at least one hormone responsive element, at least one avian CR1 repeat element, and a proximal lysozyme promoter and signal peptide-encoding region.

In an embodiment of the present invention, the transgenic avian is selected from a chicken, a turkey, a duck, a goose, a quail, a pheasant, a ratite, an ornamental bird or a feral bird.

In another embodiment of the present invention, the transgenic avian is a chicken.

In still another embodiment of the transgenic avian of the present invention, the transgenic avian includes an avian lysozyme gene expression control region comprising the nucleic acid sequence in SEQ ID NO: 67, or a degenerate variant thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In an embodiment of the transgenic avian of the present invention, the polyadenylation signal sequence comprises the nucleic acid sequence in SEQ ID NO: 68, or a degenerate variant thereof.

In another embodiment of the transgenic avian of the present invention, the nucleic acid insert encoding a polypeptide has a codon complement optimized for protein expression in an avian.

In yet another embodiment of the transgenic avian of the present invention, the nucleic acid insert encodes an interferon α2b polypeptide.

In still another embodiment of the transgenic avian of the present invention, the nucleic acid insert encoding an interferon α2b polypeptide comprises the sequence in SEQ ID NO: 66, or a degenerate variant thereof.

In one embodiment of the transgenic avian of the present invention, the transgenic avian comprises the nucleotide sequence in SEQ ID NO: 65, or a degenerate variant thereof.

In another embodiment of the transgenic avian of the present invention, the transgenic avian produces the heterologous polypeptide in the serum or an egg white.

In another embodiment of the transgenic avian of the present invention, the transgenic avian produces the heterologous polypeptide in an egg white.

The present invention is further illustrated by the following examples, which are provided by way of illustration and should not be construed as limiting. The contents of all references, published patents and patents cited throughout the present application are hereby incorporated by reference in their entireties.

EXAMPLE 1

Construction of Lysozyme Promoter Plasmids

The chicken lysozyme gene expression control region was isolated by PCR amplification. Ligation and reamplification of the fragments thereby obtained yielded a contiguous nucleic acid construct comprising the chicken lysozyme gene expression control region operably linked to a nucleic acid sequence optimized for codon usage in the chicken (SEQ ID NO: 66) and encoding a human interferon α2b polypeptide optimized for expression in an avian cell.

White Leghorn Chicken (Gallus gallus) genomic DNA was PCR amplified using the primers 5pLMAR2 (SEQ ID NO: 1) (see FIG. 1) and LE-6.1kbrev1 (SEQ ID NO: 2) in a first reaction, and Lys-6.1 (SEQ ID NO: 3) and LysE1rev (SEQ ID NO: 4) as primers in a second reaction. PCR cycling steps were: denaturation at 94° C. for 1 minute; annealing at 60° C. for 1 minute; extension at 72° C. for 6 minutes, for 30 cycles using TAQ PLUS PRECISION™ DNA polymerase (Stratagene, LaJolla, Calif.). The PCR products from these two reactions were gel purified, and then united in a third PCR reaction using only 5pLMAR2 (SEQ ID NO: 1) and LysE1rev (SEQ ID NO: 4) as primers and a 10-minute extension period. The resulting DNA product was phosphorylated, gel-purified, and cloned into the EcoR V restriction site of the vector pBluescript KS, resulting in the plasmid p12.0-lys.

p12.0-lys was used as a template in a PCR reaction with primers 5pLMAR2 (SEQ ID NO: 1) and LYSBSU (SEQ ID NO: 5) and a 10 minute extension time. The resulting DNA was phosphorylated, gel-purified, and cloned into the EcoR V restriction site of pBluescript KS, forming plasmid p12.0lys-B.

p12.0lys-B was restriction digested with Not I and Bsu36 I, gel-purified, and cloned into Not I and Bsu36 I digested pCMV-LysSPIFNMM, resulting in p12.0-lys-LSPIFNMM. p12.0-lys-LSPIFNMM was digested with Sal I and the SalltoNotI primer (SEQ ID NO: 6) was annealed to the digested plasmid, followed by Not I digestion. The resulting 12.5 kb Not I fragment, comprising the lysozyme promoter region linked to IFNMAGMAX-encoding region and an SV40 polyadenylation signal sequence, was gel-purified and ligated to Not I cleaved and dephosphorylated pBluescript KS, thereby forming the plasmid pAVIJCR-A115.93.1.2. The lysozyme promoter/IFN construct contained in the plasmid pAVIJCR-A115.93.1.2 was sequenced as described in Example 2.

EXAMPLE 2

Sequencing Reactions

Plasmid DNA (pAVIJCR-A115.93.1.2) produced as described in Example 1 was purified with QIAGEN™ columns (Qiagen, Valencia, Calif.). Sequencing reactions were performed according to the Applied Biosystems (Foster City, Calif.) protocol for BIGDYE™ Terminators, version 2.0, using an ABI 373 Stretch sequencer. The sequencing primers used are listed in FIG. 1, and a schematic diagram illustrating the sequencing reactions using the different primers is shown in FIG. 2. Sequence data was analyzed with SEQUENCHER™ software, version 4.0 (Gene Codes Corp., Ann Arbor, Mich.).

EXAMPLE 3

Complete Lysozyme Promoter and IFNMAGMAX Sequences

The complete nucleotide sequence (SEQ TD NO: 65), shown in FIG. 3, of the 12.5 kb chicken lysozyme promoter region/IFNMAGMAX construct spans the 5' matrix attachment region (5' MAR), through the lysozyme signal peptide, to the sequence encoding the gene IFNMAGMAX and the subsequent polyadenylation signal sequence. The IFNMAGMAX nucleic acid sequence (SEQ ID NO:66), shown in FIG. 4, encoded human interferon α2b (IFN) that had been synthesized based on a codon usage table compiled from the four most abundantly expressed hen egg white proteins ovalbumen, ovotransferrin, ovomucoid and lysozyme. The expressed IFN α2b sequence within plasmid pAVIJCR-A115.93.1.2 functioned as a reporter gene for lysozyme promoter activity. This plasmid construct may also be used for production of interferon α2b in the egg white of transgenic chickens. The isolated sequence of the 11.94 kb chicken lysozyme promoter region (SEQ ID NO: 67) alone is shown in FIG. 5. The sequence of the SV40polyadenylation signal sequence (SEQ ID NO: 68) is shown in FIG. 6.

EXAMPLE 4

Basic Local Alignment Search Tool (BLAST) Analysis of the Complete Lysozyme Promoter Sequence (SEQ ID NO: 65)

The complete 12.5 kb lysozyme promoter/IFNMAG-MAX sequence (SEQ ID NO: 65) was submitted to the National Center for Biotechnology Information for BLAST alignments with database sequences. Percent identities between the lysozyme promoter sequence (SEQ ID NO: 67, included within SEQ ID NO: 65) and corresponding known lysozyme promoter features are shown in Table II below:

TABLE II

BLAST Results of the Complete 12.0 kb Lysozyme Promoter Sequence

| Description of DNA element | Coordinates in this sequence | GenBank accession number | % identity |
|---|---|---|---|
| 5' matrix attachment region | 1–237, 261–1564 | AJ277960 | 96 |
| 5' matrix attachment region | 1–237, 261–1564 | X98408 | 96 |
| 5' matrix attachment region | 1564–1912 1930–2015 | X84223 | 99 |
| Intrinsically curved DNA | 2011–2671 | X52989 | 98 |
| Transcription enhancer (−6.1 kb) | 5848–5934 | Grewal et al., 1992 | 100 |
| Transcription enhancer (E-2.7 kb) | 9160–9329 | X05461 | 98 |
| Negative regulatory element | 9325–9626 | X05463 | 98 |
| Hormone response element | 9621–9666 9680–10060 | X12509 | 99 |
| CR1 chicken repeat element | 10576–10821, 10926–11193 | U88211, K02907 | 87 |
| Transcription enhancer (E-0.2 kb) | 11655–11797 | X05462 | 100 |
| Proximal promoter and lysozyme signal peptide | 11563–11877 | M12532 | 100 |
| Proximal promoter and lysozyme signal peptide | 11424–11938 | J00886 | 99 |

Features that have been previously identified as individual elements isolated from other component elements of the lysozyme promoter region include the 5' MAR, three transcription enhancers, a hormone-responsive element, and a chicken repeat 1 (CR1) element. The IFNMAGMAX sequence (SEQ ID NO: 66) extended from nucleotide positions 11946 to 12443 of SEQ ID NO: 65, shown in FIG. 3.

EXAMPLE 5

Expression in Transfected Cultured Avian Oviduct Cells of Human Interferon α2b Regulated by the 12kb Lysozyme Promoter The oviduct was removed from a Japanese quail (Coturnix coturnix japonica) and the magnum portion minced and enzymatically dissociated with 0.8 mg/mi collagenase (Sigma Chemical Co., St. Louis, Mo.) and 1.0 mg/ml dispase (Roche Molecular Biochemicals, Indianapolis, Ind.) by shaking and tiburating for 30 minutes at 370° C. The cell suspension was then filtered through sterile surgical gauze, washed three times with F-12 medium (Life Technologies, Grand Island, NY) by centrifugation at 200 ×g, and resuspended in OPTIMEM™ (Life Technologies) such that the $OD_{600}$ was approximately 2. Cell suspension (300 µl) was plated per well of a 24-well dish. For each transfection, 2.5 µl of DMRIE-C liposomes (Life Technologies) and 1 µg of DNA were preincubated for 15 minutes at room temperature in 100 µl of OPTIMEM™, and then added to the oviduct cells. Cells with DNA/liposomes were incubated for 5 hours at 37° C. in 5% $CO_2$. Next, 0.75 ml of DMEM (Life Technologies) supplemented with 15% fetal bovine serum (FBS) (Atlanta Biologicals, Atlanta, Ga.), 2X penicillin/streptomycin (Life Technologies), $10^{-6}$ M insulin (Sigma), $10^{-8}$ M β-estradiol (Sigma), and $10^{-7}$ M corticosterone (Sigma) was added to each well, and incubation was continued for 72 hours. Medium was then harvested and centrifuged at 110 ×g for 5 minutes. The supernatant was analyzed by ELISA for human interferon α2b content.

Figure 7:
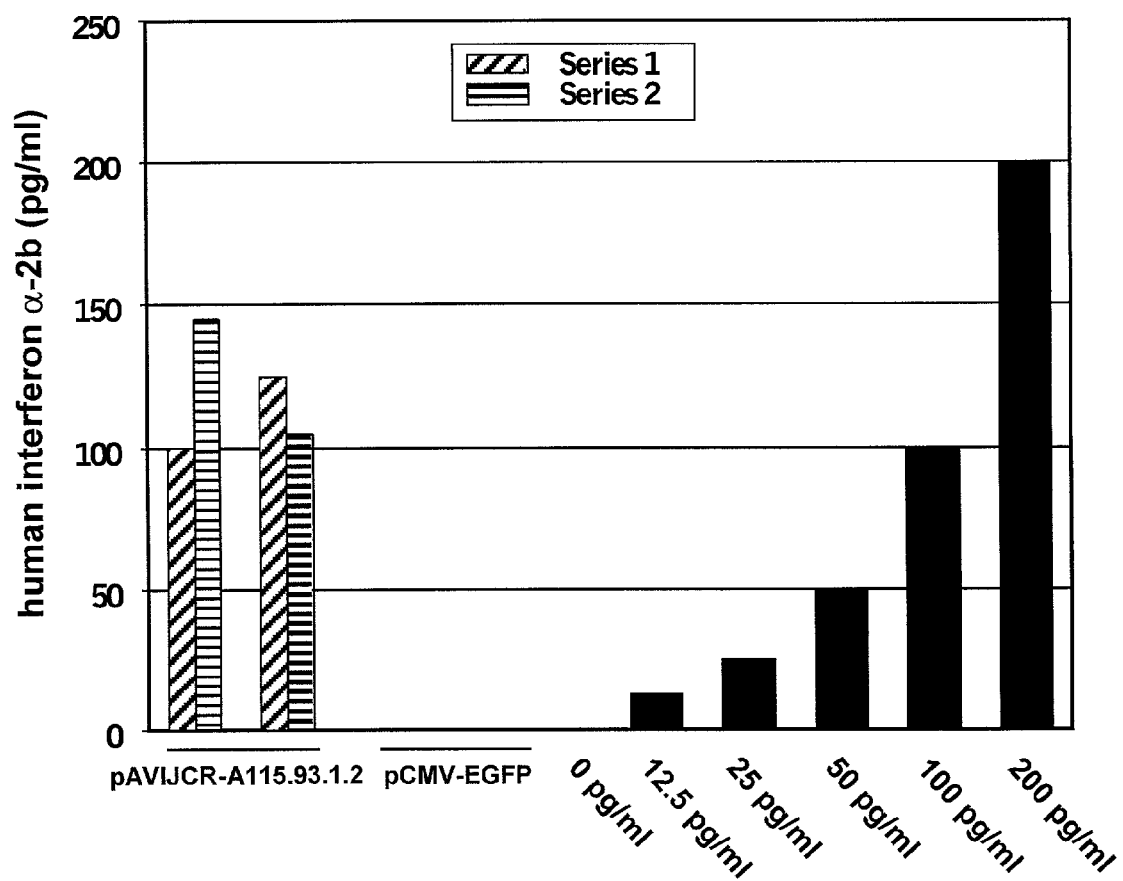
FIG. 7 illustrates the yield of the chicken expression optimized human interferon α2b (IFNMAGMAX) in transfected quail oviduct cultured cells.

The human interferon α2b contents of medium derived from cultured oviduct cells transfected with either the −12.0 kb IFN plasmid (pAVIJCR-A115.93.1.2) or the negative control plasmid pCMV-EGFP as shown in FIG. 7. Bars to the right of the figure represent the standards for the IFN ELISA.

---

What is claimed is:

1. An isolated recombinant DNA molecule comprising an avian lysozyme gene expression control region which comprises a nucleotide sequence at least 95% identical to the full length of SEQ ID NO:67.

2. The isolated DNA molecule of claim 1 wherein the nucleotide sequence is at least 99% identical to the full length of SEQ ID NO: 67.

3. The isolated DNA molecule of claim 1 wherein the nucleotide sequence is the full length of SEQ ID NO: 67.

4. The isolated DNA molecule of claim 1 comprising a 5' matrix attachment region.

5. The isolated DNA molecule of claim 1 comprising an intrinsically curved region of DNA.

6. The isolated DNA molecule of claim 1 comprising a transcription enhancer.

7. The isolated DNA molecule of claim 1 comprising a negative regulatory element.

8. The isolated DNA molecule of claim 1 comprising at least one hormone responsive element.

9. The isolated DNA molecule of claim 1 comprising an avian CRI repeat element.

10. The isolated DNA molecule of claim 1 comprising at least one of a proximal lysozyme promoter and signal peptide-encoding region.

11. The isolated DNA molecule of claim 1 comprising a polyadenylation signal sequence.

12. The isolated DNA molecule of claim 11 wherein the polyadenylation signal sequence is derived from the SV 40 virus.

13. The isolated DNA molecule of claim 1 wherein the gene expression controlling region is operably linked to a polynucleotide encoding a heterologous polypeptide.

14. The isolated DNA molecule of claim 13 wherein the heterologous polypeptide is a protein of pharmaceutical interest.

15. An isolated recombinant DNA molecule comprising a nucleotide sequence at least 95% identical to the full length of SEQ ID NO: 67 operably linked to a polynucleotide encoding a polypeptide.

16. The isolated DNA molecule of claim 15 wherein the nucleotide sequence is at least 99% identical to the full length of SEQ ID NO: 67.

17. The isolated DNA molecule of claim 15 wherein the nucleotide sequence is the full length of SEQ ID NO: 67.

18. The isolated DNA molecule of claim 15 comprising a 5' matrix attachment region.

19. The isolated DNA molecule of claim 15 comprising an intrinsically curved region of DNA.

20. The isolated DNA molecule of claim 15 comprising a transcription enhancer.

21. The isolated DNA molecule of claim 15 comprising a negative regulatory element.

22. The isolated DNA molecule of claim 15 comprising at least one hormone responsive element.

23. The isolated DNA molecule of claim 15 comprising an avian CRI repeat element.

24. The isolated DNA molecule of claim 15 comprising at least one of a proximal lysozyme promoter and signal peptide-encoding region.

25. The isolated DNA molecule of claim 15 comprising a polyadenylation signal sequence.

26. The isolated DNA molecule of claim 25 wherein the polyadenylation signal sequence is derived from the SV 40 virus.

27. An isolated recombinant DNA molecule comprising a nucleotide sequence at least 95% identical to the full length of SEQ ID NO:67 operably linked to a nucleotide sequence encoding a protein of pharmaceutical interest.

28. The isolated DNA molecule of claim 27 wherein the nucleotide sequence is at least 99% identical to the full length of SEQ ID NO:67.

29. The isolated DNA molecule of claim 27 wherein the nucleotide sequence is the full length of SEQ ID NO:67.

30. An expression vector containing a recombinant DNA molecule comprising an avian lysozyme gene expression control region comprising a nucleotide sequence at least 95% identical to the full length of SEQ D NO: 67.

31. The expression vector of claim 30 wherein the nucleotide sequence is at least 99% identical to the full length of SEQ ID NO: 67.

32. The expression vector of claim 30 wherein the nucleotide sequence is the full length of SEQ ID NO: 67.

33. The expression vector of claim 30 wherein the gene expression control region is operably linked to a polynucleotide encoding a heterologous polypeptide.

34. The expression vector of claim 33 wherein the heterologous polypeptide is a protein of pharmaceutical interest.

* * * * *

SEQUENCE LISTING

<160> NUMBER OF SEQ ID NOS: 68

<210> SEQ ID NO 1
<211> LENGTH: 20
<212> TYPE: DNA
<213> ORGANISM: Artificial Sequence
<220> FEATURE:
<223> OTHER INFORMATION: Primer 5pLMAR2

<400> SEQUENCE: 1
tgccgccttc tttgatattc                          20

-continued

```
<210> SEQ ID NO 2
<211> LENGTH: 20
<212> TYPE: DNA
<213> ORGANISM: Artificial Sequence
<220> FEATURE:
<223> OTHER INFORMATION: Primer LE-6.1kbrev1

<400> SEQUENCE: 2
ttggtggtaa ggccttttg                                           20

<210> SEQ ID NO 3
<211> LENGTH: 20
<212> TYPE: DNA
<213> ORGANISM: Artificial Sequence
<220> FEATURE:
<223> OTHER INFORMATION: Primer lys-6.1

<400> SEQUENCE: 3
ctggcaagct gtcaaaaaca                                          20

<210> SEQ ID NO 4
<211> LENGTH: 20
<212> TYPE: DNA
<213> ORGANISM: Artificial Sequence
<220> FEATURE:
<223> OTHER INFORMATION: Primer LysE1rev

<400> SEQUENCE: 4
cagctcacat cgtccaaaga                                          20

<210> SEQ ID NO 5
<211> LENGTH: 34
<212> TYPE: DNA
<213> ORGANISM: Artificial Sequence
<220> FEATURE:
<223> OTHER INFORMATION: Primer LYSBSU

<400> SEQUENCE: 5
ccccccccta aggcagccag gggcaggaag caaa                          34

<210> SEQ ID NO 6
<211> LENGTH: 12
<212> TYPE: DNA
<213> ORGANISM: Artificial Sequence
<220> FEATURE:
<223> OTHER INFORMATION: Primer SaltoNotI

<400> SEQUENCE: 6
tcgagcggcc gc                                                  12

<210> SEQ ID NO 7
<211> LENGTH: 20
<212> TYPE: DNA
<213> ORGANISM: Artificial Sequence
<220> FEATURE:
<223> OTHER INFORMATION: Primer T7

<400> SEQUENCE: 7
taatacgact cactataggg                                          20

<210> SEQ ID NO 8
<211> LENGTH: 21
<212> TYPE: DNA
<213> ORGANISM: Artificial Sequence
<220> FEATURE:
<223> OTHER INFORMATION: Primerlys61enfor1
```

```
<400> SEQUENCE: 8
cgtggtgatc aaatctttgt g                                              21

<210> SEQ ID NO 9
<211> LENGTH: 20
<212> TYPE: DNA
<213> ORGANISM: Artificial Sequence
<220> FEATURE:
<223> OTHER INFORMATION: Primer lys61enrev1

<400> SEQUENCE: 9
aggagggcac agtagggatc                                                20

<210> SEQ ID NO 10
<211> LENGTH: 19
<212> TYPE: DNA
<213> ORGANISM: Artificial Sequence
<220> FEATURE:
<223> OTHER INFORMATION: Primer 5MARfor1

<400> SEQUENCE: 10
gtggcctgtg tctgtgctt                                                 19

<210> SEQ ID NO 11
<211> LENGTH: 20
<212> TYPE: DNA
<213> ORGANISM: Artificial Sequence
<220> FEATURE:
<223> OTHER INFORMATION: Primer IFN-3rev

<400> SEQUENCE: 11
aactcctctt gaggaaagcc                                                20

<210> SEQ ID NO 12
<211> LENGTH: 20
<212> TYPE: DNA
<213> ORGANISM: Artificial Sequence
<220> FEATURE:
<223> OTHER INFORMATION: Primer lys001rev

<400> SEQUENCE: 12
tcctgtttgg gatgaatggt                                                20

<210> SEQ ID NO 13
<211> LENGTH: 20
<212> TYPE: DNA
<213> ORGANISM: Artificial Sequence
<220> FEATURE:
<223> OTHER INFORMATION: Primer lys002for

<400> SEQUENCE: 13
ctctcagaat gcccaactcc                                                20

<210> SEQ ID NO 14
<211> LENGTH: 20
<212> TYPE: DNA
<213> ORGANISM: Artificial Sequence
<220> FEATURE:
<223> OTHER INFORMATION: Primer lys003for

<400> SEQUENCE: 14
tgtattggtc tccctcctgc                                                20

<210> SEQ ID NO 15
```

```
<211> LENGTH: 20
<212> TYPE: DNA
<213> ORGANISM: Artificial Sequence
<220> FEATURE:
<223> OTHER INFORMATION: Primer lys005for

<400> SEQUENCE: 15
tgttgaaatt gcagtgtggc                                               20

<210> SEQ ID NO 16
<211> LENGTH: 20
<212> TYPE: DNA
<213> ORGANISM: Artificial Sequence
<220> FEATURE:
<223> OTHER INFORMATION: Primer lys006rev

<400> SEQUENCE: 16
tgacaatgca aatttggctc                                               20

<210> SEQ ID NO 17
<211> LENGTH: 20
<212> TYPE: DNA
<213> ORGANISM: Artificial Sequence
<220> FEATURE:
<223> OTHER INFORMATION: Primer lys007for

<400> SEQUENCE: 17
gatatccttg cagtgcccat                                               20

<210> SEQ ID NO 18
<211> LENGTH: 20
<212> TYPE: DNA
<213> ORGANISM: Artificial Sequence
<220> FEATURE:
<223> OTHER INFORMATION: Primer lys008rev

<400> SEQUENCE: 18
ggacaagcaa gtgcatcaga                                               20

<210> SEQ ID NO 19
<211> LENGTH: 20
<212> TYPE: DNA
<213> ORGANISM: Artificial Sequence
<220> FEATURE:
<223> OTHER INFORMATION: Primer lys009for

<400> SEQUENCE: 19
ctgatgtgct tcagctctgc                                               20

<210> SEQ ID NO 20
<211> LENGTH: 20
<212> TYPE: DNA
<213> ORGANISM: Artificial Sequence
<220> FEATURE:
<223> OTHER INFORMATION: Primer lys010rev

<400> SEQUENCE: 20
tccatggtgg tcaaacagaa                                               20

<210> SEQ ID NO 21
<211> LENGTH: 20
<212> TYPE: DNA
<213> ORGANISM: Artificial Sequence
<220> FEATURE:
<223> OTHER INFORMATION: Primer lys011for

<400> SEQUENCE: 21
```

```
gtactagacc aggcagccca                                              20

<210> SEQ ID NO 22
<211> LENGTH: 20
<212> TYPE: DNA
<213> ORGANISM: Artificial Sequence
<220> FEATURE:
<223> OTHER INFORMATION: Primer lys012rev

<400> SEQUENCE: 22
gtgggaagta ccacattggc                                              20

<210> SEQ ID NO 23
<211> LENGTH: 20
<212> TYPE: DNA
<213> ORGANISM: Artificial Sequence
<220> FEATURE:
<223> OTHER INFORMATION: Primer lys013for

<400> SEQUENCE: 23
cgctcaggag aaagtgaacc                                              20

<210> SEQ ID NO 24
<211> LENGTH: 20
<212> TYPE: DNA
<213> ORGANISM: Artificial Sequence
<220> FEATURE:
<223> OTHER INFORMATION: Primer lys014rev

<400> SEQUENCE: 24
cggttttgcc tttgtgtttt                                              20

<210> SEQ ID NO 25
<211> LENGTH: 20
<212> TYPE: DNA
<213> ORGANISM: Artificial Sequence
<220> FEATURE:
<223> OTHER INFORMATION: Primer lys015rev

<400> SEQUENCE: 25
aaatgctcga tttcattggg                                              20

<210> SEQ ID NO 26
<211> LENGTH: 20
<212> TYPE: DNA
<213> ORGANISM: Artificial Sequence
<220> FEATURE:
<223> OTHER INFORMATION: Primer lys016rev

<400> SEQUENCE: 26
gccaatcaga ctgcatttca                                              20

<210> SEQ ID NO 27
<211> LENGTH: 20
<212> TYPE: DNA
<213> ORGANISM: Artificial Sequence
<220> FEATURE:
<223> OTHER INFORMATION: Prmer lys017rev

<400> SEQUENCE: 27
aaccgctgaa tggaacagtc                                              20

<210> SEQ ID NO 28
<211> LENGTH: 20
<212> TYPE: DNA
```

<213> ORGANISM: Artificial Sequence
<220> FEATURE:
<223> OTHER INFORMATION: Primer lys018for

<400> SEQUENCE: 28
acacgcacat attttgctgg                                         20

<210> SEQ ID NO 29
<211> LENGTH: 20
<212> TYPE: DNA
<213> ORGANISM: Artificial Sequence
<220> FEATURE:
<223> OTHER INFORMATION: Primer lys019rev

<400> SEQUENCE: 29
caggagctgg attccttcag                                         20

<210> SEQ ID NO 30
<211> LENGTH: 20
<212> TYPE: DNA
<213> ORGANISM: Artificial Sequence
<220> FEATURE:
<223> OTHER INFORMATION: Primer lys020for

<400> SEQUENCE: 30
aaaggatgca gtcccaaatg                                         20

<210> SEQ ID NO 31
<211> LENGTH: 20
<212> TYPE: DNA
<213> ORGANISM: Artificial Sequence
<220> FEATURE:
<223> OTHER INFORMATION: Primer lys021rev

<400> SEQUENCE: 31
gcccctagac tccatcttcc                                         20

<210> SEQ ID NO 32
<211> LENGTH: 20
<212> TYPE: DNA
<213> ORGANISM: Artificial Sequence
<220> FEATURE:
<223> OTHER INFORMATION: Primer Lys022rev

<400> SEQUENCE: 32
atttgctgtg gtggatgtga                                         20

<210> SEQ ID NO 33
<211> LENGTH: 20
<212> TYPE: DNA
<213> ORGANISM: Artificial Sequence
<220> FEATURE:
<223> OTHER INFORMATION: Primer lys024for

<400> SEQUENCE: 33
ccttgcagtc cttggtttgt                                         20

<210> SEQ ID NO 34
<211> LENGTH: 20
<212> TYPE: DNA
<213> ORGANISM: Artificial Sequence
<220> FEATURE:
<223> OTHER INFORMATION: Primer lys025rev

<400> SEQUENCE: 34
atgatccttc tgatgggctg                                         20

<210> SEQ ID NO 35
<211> LENGTH: 20
<212> TYPE: DNA
<213> ORGANISM: Artificial Sequence
<220> FEATURE:
<223> OTHER INFORMATION: Primer lys026rev

<400> SEQUENCE: 35
acagtgatag cacaaggggg                                          20

<210> SEQ ID NO 36
<211> LENGTH: 20
<212> TYPE: DNA
<213> ORGANISM: Artificial Sequence
<220> FEATURE:
<223> OTHER INFORMATION: Primer lys027rev

<400> SEQUENCE: 36
gtaaacagct gcaacaggca                                          20

<210> SEQ ID NO 37
<211> LENGTH: 21
<212> TYPE: DNA
<213> ORGANISM: Artificial Sequence
<220> FEATURE:
<223> OTHER INFORMATION: Primer lys028rev

<400> SEQUENCE: 37
caacacaaaa gttggacagc a                                        21

<210> SEQ ID NO 38
<211> LENGTH: 20
<212> TYPE: DNA
<213> ORGANISM: Artificial Sequence
<220> FEATURE:
<223> OTHER INFORMATION: Primer lys030rev

<400> SEQUENCE: 38
tttgcagatg agacgtttgc                                          20

<210> SEQ ID NO 39
<211> LENGTH: 20
<212> TYPE: DNA
<213> ORGANISM: Artificial Sequence
<220> FEATURE:
<223> OTHER INFORMATION: Primer lys030rev

<400> SEQUENCE: 39
ccacaagttc ttgtttgggc                                          20

<210> SEQ ID NO 40
<211> LENGTH: 20
<212> TYPE: DNA
<213> ORGANISM: Artificial Sequence
<220> FEATURE:
<223> OTHER INFORMATION: Primer lys031rev

<400> SEQUENCE: 40
atcaatccat gccagtagcc                                          20

<210> SEQ ID NO 41
<211> LENGTH: 20
<212> TYPE: DNA
<213> ORGANISM: Artificial Sequence
<220> FEATURE:

<223> OTHER INFORMATION: Primer lys032rev

<400> SEQUENCE: 41
gtttaaggcc ccttccaatc          20

<210> SEQ ID NO 42
<211> LENGTH: 20
<212> TYPE: DNA
<213> ORGANISM: Artificial Sequence
<220> FEATURE:
<223> OTHER INFORMATION: Primer lys033for

<400> SEQUENCE: 42 gagaggggt tgggtgtatt          20

<210> SEQ ID NO 43
<211> LENGTH: 20
<212> TYPE: DNA
<213> ORGANISM: Artificial Sequence
<220> FEATURE:
<223> OTHER INFORMATION: Primer lys034for

<400> SEQUENCE: 43
acagtggaag cattcaaggg          20

<210> SEQ ID NO 44
<211> LENGTH: 20
<212> TYPE: DNA
<213> ORGANISM: Artificial Sequence
<220> FEATURE:
<223> OTHER INFORMATION: Primer lys037for

<400> SEQUENCE: 44
ccaatgcctt tggttctgat          20

<210> SEQ ID NO 45
<211> LENGTH: 20
<212> TYPE: DNA
<213> ORGANISM: Artificial Sequence
<220> FEATURE:
<223> OTHER INFORMATION: Primer lys038for

<400> SEQUENCE: 45
aaaacacaaa ggcaaaaccg          20

<210> SEQ ID NO 46
<211> LENGTH: 20
<212> TYPE: DNA
<213> ORGANISM: Artificial Sequence
<220> FEATURE:
<223> OTHER INFORMATION: Primer lys039rev

<400> SEQUENCE: 46
ctaagcctcg ccagtttcaa          20

<210> SEQ ID NO 47
<211> LENGTH: 20
<212> TYPE: DNA
<213> ORGANISM: Artificial Sequence
<220> FEATURE:
<223> OTHER INFORMATION: Primer lys040rev

<400> SEQUENCE: 47
tgccatgaaa accctactga          20

```
<210> SEQ ID NO 48
<211> LENGTH: 20
<212> TYPE: DNA
<213> ORGANISM: Artificial Sequence
<220> FEATURE:
<223> OTHER INFORMATION: Primer lys041for

<400> SEQUENCE: 48
ggaatgtacc ctcagctcca                                            20

<210> SEQ ID NO 49
<211> LENGTH: 20
<212> TYPE: DNA
<213> ORGANISM: Artificial Sequence
<220> FEATURE:
<223> OTHER INFORMATION: Primer lys042rev

<400> SEQUENCE: 49
cctctttagg aggccagctt                                            20

<210> SEQ ID NO 50
<211> LENGTH: 20
<212> TYPE: DNA
<213> ORGANISM: Artificial Sequence
<220> FEATURE:
<223> OTHER INFORMATION: Primer lys043rev

<400> SEQUENCE: 50
aagatgatca gagggctgga                                            20

<210> SEQ ID NO 51
<211> LENGTH: 20
<212> TYPE: DNA
<213> ORGANISM: Artificial Sequence
<220> FEATURE:
<223> OTHER INFORMATION: Primer lys044rev

<400> SEQUENCE: 51
gcagcgctgg taatcttcat                                            20

<210> SEQ ID NO 52
<211> LENGTH: 20
<212> TYPE: DNA
<213> ORGANISM: Artificial Sequence
<220> FEATURE:
<223> OTHER INFORMATION: Primer lys045for

<400> SEQUENCE: 52
cttcagatcc caggaagtgc                                            20

<210> SEQ ID NO 53
<211> LENGTH: 20
<212> TYPE: DNA
<213> ORGANISM: Artificial Sequence
<220> FEATURE:
<223> OTHER INFORMATION: Primer lys46for

<400> SEQUENCE: 53
ttcctgcctt acattctggg                                            20

<210> SEQ ID NO 54
<211> LENGTH: 20
<212> TYPE: DNA
<213> ORGANISM: Artificial Sequence
<220> FEATURE:
<223> OTHER INFORMATION: Primer lys047for
```

-continued

<400> SEQUENCE: 54
cccactgcag gcttagaaag          20

<210> SEQ ID NO 55
<211> LENGTH: 20
<212> TYPE: DNA
<213> ORGANISM: Artificial Sequence
<220> FEATURE:
<223> OTHER INFORMATION: Primer lys048for

<400> SEQUENCE: 55
agttctccat agcggctgaa          20

<210> SEQ ID NO 56
<211> LENGTH: 20
<212> TYPE: DNA
<213> ORGANISM: Artificial Sequence
<220> FEATURE:
<223> OTHER INFORMATION: Primer lys051for

<400> SEQUENCE: 56
tgcatccttc agcacttgag          20

<210> SEQ ID NO 57
<211> LENGTH: 20
<212> TYPE: DNA
<213> ORGANISM: Artificial Sequence
<220> FEATURE:
<223> OTHER INFORMATION: Primer lys052rev

<400> SEQUENCE: 57
gcaggaggga gaccaataca          20

<210> SEQ ID NO 58
<211> LENGTH: 20
<212> TYPE: DNA
<213> ORGANISM: Artificial Sequence
<220> FEATURE:
<223> OTHER INFORMATION: Primer lys053for

<400> SEQUENCE: 58
tgcacaagga tgtctgggta          20

<210> SEQ ID NO 59
<211> LENGTH: 20
<212> TYPE: DNA
<213> ORGANISM: Artificial Sequence
<220> FEATURE:
<223> OTHER INFORMATION: Primer lys054for

<400> SEQUENCE: 59
tcctagcaac tgcggatttt          20

<210> SEQ ID NO 60
<211> LENGTH: 20
<212> TYPE: DNA
<213> ORGANISM: Artificial Sequence
<220> FEATURE:
<223> OTHER INFORMATION: Primer lys056for

<400> SEQUENCE: 60
tcttccatgt tggtgacagc          20

<210> SEQ ID NO 61
<211> LENGTH: 20

```
<212> TYPE: DNA
<213> ORGANISM: Artificial Sequence
<220> FEATURE:
<223> OTHER INFORMATION: Primer lys058for

<400> SEQUENCE: 61 ccccttgtg ctatcactgt                                              20

<210> SEQ ID NO 62
<211> LENGTH: 20
<212> TYPE: DNA
<213> ORGANISM: Artificial Sequence
<220> FEATURE:
<223> OTHER INFORMATION: Primer lys059for

<400> SEQUENCE: 62
ctgacagaca tcccagctca                                             20

<210> SEQ ID NO 63
<211> LENGTH: 20
<212> TYPE: DNA
<213> ORGANISM: Artificial Sequence
<220> FEATURE:
<223> OTHER INFORMATION: Primer lys060for

<400> SEQUENCE: 63
aagttgtgct tctgcgtgtg                                             20

<210> SEQ ID NO 64
<211> LENGTH: 20
<212> TYPE: DNA
<213> ORGANISM: Artificial Sequence
<220> FEATURE:
<223> OTHER INFORMATION: Primer lys061for

<400> SEQUENCE: 64
ttgttcctgc tgttcctcct                                             20

<210> SEQ ID NO 65
<211> LENGTH: 12728
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription Enhancer
<220> FEATURE:
```

```
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11946)..(12443)
<223> OTHER INFORMATION: Human Interferon alpha 2d encoding region codon
      optimized for expression in chicken cells (IFNMAGMAX)
<220> FEATURE:
<221> NAME/KEY: polyA_signal
<222> LOCATION: (12444)..(12728)
<223> OTHER INFORMATION:

<400> SEQUENCE: 65
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttcttttttc ttagtaaatt ttctactgga     300
ctgtatgttt tgacaggtca gaaacatttc ttcaaaagaa gaaccttttg gaaactgtac     360 agccctttttc tttcattccc ttttttgcttt ctgtgccaat gcctttggtt ctgattgcat     420
tatggaaaac gttgatcgga acttgaggtt tttatttata gtgtggcttg aaagcttgga     480
tagctgttgt tacacgagat accttattaa gtttaggcca gcttgatgct ttattttttc     540
cctttgaagt agtgagcgtt ctctggtttt tttcctttga aactggtgag cttagatttt     600
ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttttatc     780 tctatgctct gtgtgtacag gtcaaacaga cttcactcct atttttattt atagaatttt     840
atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
```

-continued

```
tgatgcctgg atgcctgttg cagctgttta cggcactgcc ttgcagtgag cattgcagat    1260 agggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct ttttccat gttgggcaaa    1440 gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat ttcagttgta aaagaattcc gcctattcat    1680
accatgtaat gtaattttac accccagtg ctgacactt ggaatatatt caagtaatag    1740
actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920 aaaaaaaag taatataaaa aggaccaggt gttttacaag tgaaatacat tcctatttgg    1980
taaacagtta cattttatg aagattacca gcgctgctga ctttctaaac ataaggctgt    2040
attgtcttcc tgtaccattg catttcctca ttcccaattt gcacaaggat gtctgggtaa    2100
actattcaag aaatggcttt gaaatacagc atggagctt gtctgagttg aatgcagag    2160 ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
ttaatacatt ttcagcagaa gtacttagtt aatctctacc tttagggatc gtttcatcat    2400
ttttagatgt tatacttgaa atactgcata acttttagct ttcatgggtt ccttttttc    2460 agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttctgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata cttttttaaa gtcaacttt    2820 tatcagattt ttttttcatt tggaaatata ttgttttcta gactgcatag cttctgaatc    2880
tgaaatgcag tctgattggc atgaagaagc acagcactct tcatcttact taaacttcat    2940 tttgaatga aggaagttaa gcaagggcac aggtccatga aatagagaca gtgcgctcag    3000
gagaaagtga acctggattt cttttggctag tgttctaaat ctgtagtgag aaagtaaca    3060 cccgattcct tgaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tatttttaag tactgtgttg caaacgtctc atctgcaaat    3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaaggtaag cagtcttcat atgttttccc tccacgtaaa    3540
```

-continued

| | | | | |
|---|---|---|---|---|
| gcagtctggg | aaagtagcac | cccttgagca | gagacaagga | aataattcag | gagcatgtgc | 3600 |
| taggagaact | ttcttgctga | attctacttg | caagagcttt | gatgcctggc | ttctggtgcc | 3660 |
| ttctgcagca | cctgcaaggc | ccagagcctg | tggtgagctg | gagggaaaga | ttctgctcaa | 3720 |
| gtccaagctt | cagcaggtca | ttgtctttgc | ttcttcccccc | agcactgtgc | agcagagtgg | 3780 |
| aactgatgtc | gaagcctcct | gtccactacc | tgttgctgca | ggcagactgc | tctcagaaaa | 3840 |
| agagagctaa | ctctatgcca | tagtctgaag | gtaaaatggg | ttttaaaaaa | gaaaacacaa | 3900 |
| aggcaaaacc | ggctgcccca | tgagaagaaa | gcagtggtaa | acatggtaga | aaaggtgcag | 3960 |
| aagcccccag | gcagtgtgac | aggcccctcc | tgccacctag | aggcgggaac | aagcttccct | 4020 |
| gcctagggct | ctgcccgcga | agtgcgtgtt | tctttggtgg | gttttgtttg | gcgtttggtt | 4080 |
| ttgagattta | gacacaaggg | aagcctgaaa | ggaggtgttg | ggcactattt | tggtttgtaa | 4140 |
| agcctgtact | tcaaatatat | attttgtgag | ggagtgtagc | gaattggcca | atttaaaata | 4200 |
| aagttgcaag | agattgaagg | ctgagtagtt | gagagggtaa | cacgtttaat | gagatcttct | 4260 |
| gaaactactg | cttctaaaca | cttgtttgag | tggtgagacc | ttggataggt | gagtgctctt | 4320 |
| gttacatgtc | tgatgcactt | gcttgtcctt | ttccatccac | atccatgcat | tccacatcca | 4380 |
| cgcatttgtc | acttatccca | tatctgtcat | atctgacata | cctgtctctt | cgtcacttgg | 4440 |
| tcagaagaaa | cagatgtgat | aatccccagc | cgccccaagt | ttgagaagat | ggcagttgct | 4500 |
| tctttcccctt | tttcctgcta | agtaaggatt | ttctcctggc | tttgacacct | cacgaaatag | 4560 |
| tcttcctgcc | ttacattctg | ggcattattt | caaatatctt | tggagtgcgc | tgctctcaag | 4620 |
| tttgtgtctt | cctactctta | gagtgaatgc | tcttagagtg | aaagagaagg | aagagaagat | 4680 |
| gttggccgca | gttctctgat | gaacacacct | ctgaataatg | gccaaaggtg | ggtgggtttc | 4740 |
| tctgaggaac | gggcagcgtt | tgcctctgaa | agcaaggagc | tctgcggagt | tgcagttatt | 4800 |
| ttgcaactga | tggtggaact | ggtgcttaaa | gcagattccc | taggttccct | gctacttctt | 4860 |
| ttccttcttg | gcagtcagtt | tatttctgac | agacaaacag | ccaccccccac | tgcaggctta | 4920 |
| gaaagtatgt | ggctctgcct | gggtgtgtta | cagctctgcc | ctggtgaaag | gggattaaaa | 4980 |
| cgggcaccat | tcatcccaaa | caggatcctc | attcatggat | caagctgtaa | ggaacttggg | 5040 |
| ctccaacctc | aaaacattaa | ttggagtacg | aatgtaatta | aaactgcatt | ctcgcattcc | 5100 |
| taagtcattt | agtctggact | ctgcagcatg | taggtcggca | gctcccactt | tctcaaagac | 5160 |
| cactgatgga | ggagtagtaa | aaatggagac | cgattcagaa | caaccaacgg | agtgttgccg | 5220 |
| aagaaactga | tggaaataat | gcatgaattg | tgtggtggac | attttttta | aatacataaa | 5280 |
| ctacttcaaa | tgaggtcgga | gaaggtcagt | gttttattag | cagccataaa | accaggtgag | 5340 |
| cgagtaccat | ttttctctac | aagaaaaacg | attctgagct | ctgcgtaagt | ataagttctc | 5400 |
| catagcggct | gaagctcccc | cctggctgcc | tgccatctca | gctggagtgc | agtgccattt | 5460 |
| ccttggggtt | tctctcacag | cagtaatggg | acaatacttc | acaaaaattc | tttcttttcc | 5520 |
| tgtcatgtgg | gatccctact | gtgccctcct | ggttttacgt | taccccctga | ctgttccatt | 5580 |
| cagcggtttg | gaaagagaaa | aagaatttgg | aaataaaaca | tgtctacgtt | atcacctcct | 5640 |
| ccagcatttt | ggttttttaat | tatgtcaata | actggcttag | atttggaaat | gagagggggt | 5700 |
| tgggtgtatt | accgaggaac | aaaggaaggc | ttatataaac | tcaagtctttt | tatttagaga | 5760 |
| actggcaagc | tgtcaaaaac | aaaaaggcct | taccaccaaa | ttaagtgaat | agccgctata | 5820 |
| gccagcaggg | ccagcacgag | ggatggtgca | ctgctggcac | tatgccacgg | cctgcttgtg | 5880 |
| actctgagag | caactgcttt | ggaaatgaca | gcacttggtg | caatttcctt | tgtttcagaa | 5940 |

```
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttattttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta aatacagcc tggggtaaga     6300
agttcagtct cctgctggga cagctaaccg catcttataa ccccttctga gactcatctt    6360
aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt ccttcccca    6540
ctgtgtttaa cccctaagg cattcagaac aactagaatc atagaatggt ttggattgga     6600
agggccttaa acatcatcc atttccaacc ctctgccatg ggctgcttgc cacccactgg    6660
ctcaggctgc ccagggcccc atccagcctg gccttgagca cctccaggga tgggcaccc    6720
acagcttctc tgggcagcct gtgccaacac ctcaccactc tctgggtaaa gaattctctt   6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccctg ctgatttgtg tcaagctttt     7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtaccct ccaagctgcg gcctcccata aatcctgtat ttgggatcag    7500
ttaccttttg gggtaagctt ttgtatctgc agagaccctg ggggtctga tgtgcttcag     7560
ctctgctctg ttctgactgc accattttct agatcaccca gttgttcctg tacaacttcc    7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca caagaaaaga gattcctttt ttattacttc    8040
tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccaccctt gcagtccttg gtttgtaaga taagtcatag gtaactttc tggtgaattg     8280
```

```
cgtggagaat catgatggca gttcttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatctt cttcacatca tcaaaccttt ggcctgactg atgcctcccg    8580
gatgcttaaa tgtggtcact gacatcttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
ttttcttcc tgctgtcagg aacattttga ataccagaga aaagaaaag tgctcttctt    8820
ggcatgggag gagttgtcac acttgcaaaa taaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc    9060
cgctgaagga atccagctcc tgtttgagca ggtgctgcac actcccacac tgaaacaaca    9120
gttcattttt ataggacttc caggaaggat cttcttctta agcttcttaa ttatggtaca    9180
tctccagttg gcagatgact atgactactg acaggagaat gaggaactag ctgggaatat    9240
ttctgtttga ccaccatgga gtcacccatt tctttactgg tatttggaaa taataattct    9300
gaattgcaaa gcaggagtta gcgaagatct tcatttcttc catgttggtg acagcacagt    9360
tctggctatg aaagtctgct tacaaggaag aggataaaaa tcatagggat aataaatcta    9420
agtttgaaga caatgaggtt ttagctgcat ttgacatgaa gaaattgaga cctctactgg    9480
atagctatgg tatttacgtg tctttttgct tagttactta ttgaccccag ctgaggtcaa    9540
gtatgaactc aggtctctcg ggctactggc atggattgat tacatacaac tgtaatttta    9600
gcagtgattt agggtttatg agtacttttg cagtaaatca taggggttagt aatgttaatc    9660
tcagggaaaa aaaaaaaag ccaaccctga cagacatccc agctcaggtg gaaatcaagg    9720
atcacagctc agtgcggtcc cagagaacac agggactctt ctcttaggac ctttatgtac    9780
agggcctcaa gataactgat gttagtcaga agactttcca ttctggccac agttcagctg    9840
aggcaatcct ggaattttct ctccgctgca cagttccagt catcccagtt tgtacagttc    9900
tggcactttt tgggtcaggc cgtgatccaa ggagcagaag ttccagctat ggtcagggag    9960
tgcctgaccg tcccaactca ctgcactcaa acaaaggcga aaccacaaga gtggcttttg   10020
ttgaaattgc agtgtggccc agagggggctg caccagtact ggattgacca cgaggcaaca   10080
ttaatcctca gcaagtgcaa tttgcagcca ttaaattgaa ctaactgata ctacaatgca   10140
atcagtatca acaagtggtt tggcttggaa gatggagtct aggggctcta caggagtagc   10200
tactctctaa tggagttgca ttttgaagca ggacactgtg aaaagctggc ctcctaaaga   10260
ggctgctaaa cattagggtc aattttccag tgcactttct gaagtgtctg cagttcccca   10320
tgcaaagctg cccaaacata gcacttccaa ttgaatacaa ttatatgcag gcgtactgct   10380
tcttgccagc actgtccttc tcaaatgaac tcaacaaaca atttcaaagt ctagtagaaa   10440
gtaacaagct ttgaatgtca ttaaaaagta tatctgcttt cagtagttca gcttatttat   10500
gcccactaga aacatcttgt acaagctgaa cactgggggct ccagattagt ggtaaaacct   10560
actttataca atcatagaat catagaatgg cctgggttgg aagggacccc aaggatcatg   10620
aagatccaac accccccgcca caggcagggc caccaacctc cagatctggt actagaccag   10680
```

-continued

```
gcagcccagg gctccatcca acctggccat gaacacctcc agggatggag catccacaac    10740
ctctctgggc agcctgtgcc agcacctcac cacctctct gtgaagaact tttccctgac     10800
atccaatcta agccttccct ccttgaggtt agatccactc ccccttgtgc tatcactgtc    10860
tactcttgta aaagttgat tctcctcctt tttggaaggt tgcaatgagg tctccttgca     10920
gccttcttct cttctgcagg atgaacaagc ccagctccct cagcctgtct ttataggaga    10980
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta agagggaca atcaccttcc tcaccctgct ggccagccct cttctgatgg     11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgataccte acccccctg ccactgaatg gctccatggc cccctgcagc     11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttga caactgtaga acagaggaat caaaaggggg     11820
tgggaggaag ttaaagaag aggcaggtgc aagagagctt gcagtcccgc tgtgtgtacg     11880
acactggcaa catgaggtct ttgctaatct tggtgctttg cttcctgccc ctggctgcct    11940
tagggtgcga tctgcctcag acccacagcc tgggcagcag gaggaccctg atgctgctgg    12000
ctcagatgag gagaatcagc ctgtttagct gcctgaagga taggcacgat tttggctttc    12060
ctcaagagga gtttggcaac cagtttcaga aggctgagac catccctgtg ctgcacgaga    12120
tgatccagca gatctttaac ctgtttagca ccaaggatag cagcgctgct tgggatgaga    12180
ccctgctgga taagttttac accgagctgt accagcagct gaacgatctg gaggcttgcg    12240
tgatccaggg cgtgggcgtg accgagaccc tctgatgaa ggaggatagc atcctggctg     12300
tgaggaagta ctttcagagg atcaccctgt acctgaagga gaagaagtac agcccctgcg    12360
cttgggaagt cgtgagggct gagatcatga ggagctttag cctgagcacc aacctgcaag    12420
agagcttgag gtctaaggag taaaaagtct agagtcgggg cggccggccg cttcgagcag    12480
acatgataag atacattgat gagtttggac aaaccacaac tagaatgcag tgaaaaaat    12540 gctttatttg tgaaatttgt gatgctattg ctttatttgt aaccattata agctgcaata    12600
aacaagttaa caacaacaat tgcattcatt ttatgtttca ggttcagggg gaggtgtggg    12660 aggttttta aagcaagtaa aacctctaca aatgtggtaa aatcgataag gatccgtcga    12720
gcggccgc                                                            12728
```

<210> SEQ ID NO 66
<211> LENGTH: 498
<212> TYPE: DNA
<213> ORGANISM: Artificial Sequence
<220> FEATURE:
<223> OTHER INFORMATION: IFNMAGMAX
<220> FEATURE:

```
<221> NAME/KEY: misc_feature
<222> LOCATION: (1)..(498)
<223> OTHER INFORMATION:

<400> SEQUENCE: 66
tgcgatctgc ctcagaccca cagcctgggc agcaggagga ccctgatgct gctggctcag      60
atgaggagaa tcagcctgtt tagctgcctg aaggataggc acgatttttgg ctttcctcaa    120 gaggagtttg gcaaccagtt tcagaaggct gagaccatcc ctgtgctgca cgagatgatc     180
cagcagatct ttaacctgtt tagcaccaag gatagcagcg ctgcttggga tgagaccctg    240
ctggataagt tttacaccga gctgtaccag cagctgaacg atctggaggc ttgcgtgatc   300
cagggcgtgg gcgtgaccga gacccctctg atgaaggagg atagcatcct ggctgtgagg   360
aagtactttc agaggatcac cctgtacctg aaggagaaga agtacagccc ctgcgcttgg   420
gaagtcgtga gggctgagat catgaggagc tttagcctga gcaccaacct gcaagagagc   480
ttgaggtcta aggagtaa                                                  498

<210> SEQ ID NO 67
<211> LENGTH: 11945
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix attachment region (MAR)
<220> FEATURE:
<221> NAME/KEY: misc_feature
<222> LOCATION: (261)..(1564)
<223> OTHER INFORMATION: 5prime matrix attachment region (MAR)
<220> FEATURE:
<221> NAME/KEY: misc_feature
<222> LOCATION: (1565)..(1912)
<223> OTHER INFORMATION: 5prime matrix attachment region (MAR)
<220> FEATURE:
<221> NAME/KEY: misc_feature
<222> LOCATION: (1930)..(2012)
<223> OTHER INFORMATION: 5prime matrix attachment region (MAR)
<220> FEATURE:
<221> NAME/KEY: misc_feature
<222> LOCATION: (2013)..(2671)
<223> OTHER INFORMATION: Intrinsically Curved DNA
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat
<220> FEATURE:
<221> NAME/KEY: misc_feature
<222> LOCATION: (10926)..(11193)
<223> OTHER INFORMATION: Chicken CR1 Repeat
<220> FEATURE:
<221> NAME/KEY: misc_feature
```

<222> LOCATION: (11424)..(11938)
<223> OTHER INFORMATION: Proximal promoter and lysozyme signal peptide

<400> SEQUENCE: 67

```
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttcttttttc ttagtaaatt ttctactgga     300
ctgtatgttt tgacaggtca gaaacatttc ttcaaaagaa gaaccttttg gaaactgtac     360
agcccttttc tttcattccc ttttgctttt ctgtgccaat gcctttggtt ctgattgcat     420
tatggaaaac gttgatcgga acttgaggtt tttatttata gtgtggcttg aaagcttgga     480
tagctgttgt tacacgagat accttattaa gtttaggcca gcttgatgct ttatttttc     540
cctttgaagt agtgagcgtt ctctggtttt tttcctttga aactggtgag cttagatttt     600
ttctaatggg atttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttatc     780
tctatgctct gtgtgtacag gtcaaacaga cttcactcct attttattt atagaatttt     840
atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
tgatgcctgg atgcctgttg cagctgttta cggcactgcc ttgcagtgag cattgcagat    1260
aggggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct ttttttccat gttgggcaaa    1440
gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat tcagttgta aaagaattcc gcctattcat    1680
accatgtaat gtaattttac accccagtg ctgacacttt ggaatatatt caagtaatag    1740
actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920
aaaaaaaag taatataaaa aggaccaggt gttttacaag tgaaatacat tcctatttgg    1980
taaacagtta cattttatg aagattacca gcgctgctga ctttctaaac ataaggctgt    2040
attgtcttcc tgtaccattg catttcctca ttcccaattt gcacaaggat gtctgggtaa    2100
actattcaag aaatggcttt gaaatacagc atgggagctt gtctgagttg gaatgcagag    2160
ttgcactgca aaatgtcagg aaatggatgt ctctcagaat gcccaactcc aaaggatttt    2220
```

-continued

```
atatgtgtat atagtaagca gtttcctgat tccagcaggc caaagagtct gctgaatgtt   2280
gtgttgccgg agacctgtat ttctcaacaa ggtaagatgg tatcctagca actgcggatt   2340
ttaatacatt ttcagcagaa gtacttagtt aatctctacc tttagggatc gtttcatcat   2400
ttttagatgt tatacttgaa atactgcata acttttagct ttcatgggtt cctttttttc   2460
agcctttagg agactgttaa gcaatttgct gtccaacttt tgtgttggtc ttaaactgca   2520
atagtagttt accttgtatt gaagaaataa agaccatttt tatattaaaa aatacttttg   2580
tctgtcttca ttttgacttg tctgatatcc ttgcagtgcc cattatgtca gttctgtcag   2640
atattcagac atcaaaactt aacgtgagct cagtggagtt acagctgcgg ttttgatgct   2700
gttattattt ctgaaactag aaatgatgtt gtcttcatct gctcatcaaa cacttcatgc   2760
agagtgtaag gctagtgaga aatgcataca tttattgata cttttttaaa gtcaacttttt   2820
tatcagattt ttttttcatt tggaaatata ttgttttcta gactgcatag cttctgaatc   2880
tgaaatgcag tctgattggc atgaagaagc acagcactct tcatcttact taaacttcat   2940
tttggaatga aggaagttaa gcaagggcac aggtccatga aatagagaca gtgcgctcag   3000
gagaaagtga acctggatttt ctttggctag tgttctaaat ctgtagtgag gaaagtaaca   3060
cccgattcct tgaaagggct ccagctttaa tgcttccaaa ttgaaggtgg caggcaactt   3120
ggccactggt tatttactgc attatgtctc agtttcgcag ctaacctggc ttctccacta   3180
ttgagcatgg actatagcct ggcttcagag gccaggtgaa ggttgggatg ggtggaagga   3240
gtgctgggct gtggctgggg ggactgtggg gactccaagc tgagcttggg gtgggcagca   3300
cagggaaaag tgtgggtaac tatttttaag tactgtgttg caaacgtctc atctgcaaat   3360
acgtagggtg tgtactctcg aagattaaca gtgtgggttc agtaatatat ggatgaattc   3420
acagtggaag cattcaaggg tagatcatct aacgacacca gatcatcaag ctatgattgg   3480
aagcggtatc agaagagcga ggaagtaag cagtcttcat atgttttccc tccacgtaaa   3540
gcagtctggg aaagtagcac cccttgagca gagacaagga ataattcag gagcatgtgc   3600
taggagaact tcttgctga attctacttg caagagcttt gatgcctggc ttctggtgcc   3660
ttctgcagca cctgcaaggc ccagagcctg tggtgagctg gagggaaaga ttctgctcaa   3720
gtccaagctt cagcaggtca ttgtcttttgc ttcttcccccc agcactgtgc agcagagtgg   3780
aactgatgtc gaagcctcct gtccactacc tgttgctgca ggcagactgc tctcagaaaa   3840
agagagctaa ctctatgcca tagtctgaag gtaaaatggg ttttaaaaaa gaaaacacaa   3900
aggcaaaacc ggctgcccca tgagaagaaa gcagtggtaa acatggtaga aaaggtgcag   3960
aagcccccag gcagtgtgac aggcccctcc tgccacctag aggcgggaac aagcttccct   4020
gcctagggct ctgcccgcga agtgcgtgtt tctttggtgg gttttgtttg gcgtttggtt   4080
ttgagattta gacacaaggg aagcctgaaa ggaggtgttg ggcactatttt tggtttgtaa   4140
agcctgtact tcaaatatat attttgtgag ggagtgtagc gaattggcca atttaaaata   4200
aagttgcaag agattgaagg ctgagtagtt gagagggtaa cacgtttaat gagatcttct   4260
gaaactactg cttctaaaca cttgtttgag tggtgagacc ttggataggt gagtgctctt   4320
gttacatgtc tgatgcactt gcttgtcctt ttccatccac atccatgcat tccacatcca   4380
cgcatttgtc acttatccca tatctgtcat atctgacata cctgtctctt cgtcacttgg   4440
tcagaagaaa cagatgtgat aatccccagc cgccccaagt ttgagaagat ggcagttgct   4500
tctttcccctt tttcctgcta agtaaggatt ttctcctggc tttgacacct cacgaaatag   4560
tcttcctgcc ttacattctg ggcattattt caaatatctt tggagtgcgc tgctctcaag   4620
```

```
tttgtgtctt cctactctta gagtgaatgc tcttagagtg aaagagaagg aagagaagat    4680
gttggccgca gttctctgat gaacacacct ctgaataatg gccaaaggtg ggtgggtttc    4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta     4920 gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa     5280 ctacttcaaa tgaggtcgga aaggtcagt gttttattag cagccataaa accaggtgag      5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt tacccctga ctgttccatt     5580 cagcggtttg gaaagagaaa aagaatttgg aaataaaaca tgtctacgtt atcacctcct    5640
ccagcatttt ggtttttaat tatgtcaata actggcttag atttgaaat gagagggggt     5700 tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttattttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa ccccttctga gactcatctt    6360
aggaccaaat agggtctatc tgggttttt gttcctgctg ttcctcctgg aaggctatct     6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa ccccttaagg cattcagaac aactagaatc atagaatggt ttggattgga    6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
```

-continued

```
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccttg ctgatttgtg tcaagctttt     7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata atcctgtat ttgggatcag     7500 ttaccttttg gggtaagctt ttgtatctgc agagaccctg ggggttctga tgtgcttcag    7560
ctctgctctg ttctgactgc accatttttct agatcaccca gttgttcctg tacaacttcc   7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca caagaaaaga gattccttt ttattacttc     8040 tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaacttttc tggtgaattg    8280
cgtggagaat catgatggca gttcttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatctt cttcacatca tcaaaccttt ggcctgactg atgcctcccg    8580
gatgcttaaa tgtggtcact gacatcttta ttttctatg atttcaagtc agaacctccg     8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
tttttcttcc tgctgtcagg aacattttga ataccagaga aaagaaaag tgctcttctt     8820 ggcatgggag gagttgtcac acttgcaaaa taaaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc    9060
cgctgaagga atccagctcc tgtttgagca ggtgctgcac actcccacac tgaaacaaca    9120
gttcattttt ataggacttc caggaaggat cttcttctta agcttcttaa ttatggtaca    9180
tctccagttg gcagatgact atgactactg acaggagaat gaggaactag ctgggaatat    9240
ttctgtttga ccaccatgga gtcacccatt tctttactgg tatttggaaa taataattct    9300
gaattgcaaa gcaggagtta gcgaagatct tcatttcttc catgttggtg acagcacagt    9360
```

```
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
atagctatgg tatttacgtg tcttttgct tagttactta ttgacccag ctgaggtcaa    9540
gtatgaactc aggtctctcg ggctactggc atggattgat tacatacaac tgtaattta   9600
gcagtgattt agggtttatg agtacttttg cagtaaatca tagggttagt aatgttaatc   9660
tcagggaaaa aaaaaaaag ccaaccctga cagacatccc agctcaggtg gaaatcaagg    9720
atcacagctc agtgcggtcc cagagaacac agggactctt ctcttaggac ctttatgtac   9780
agggcctcaa gataactgat gttagtcaga agactttcca ttctgccac agttcagctg    9840
aggcaatcct ggaatttct ctccgctgca cagttccagt catcccagtt tgtacagttc    9900
tggcactttt tgggtcaggc cgtgatccaa ggagcagaag ttccagctat ggtcagggag   9960
tgcctgaccg tcccaactca ctgcactcaa acaaaggcga aaccacaaga gtggctttg   10020
ttgaaattgc agtgtggccc agaggggctg caccagtact ggattgacca cgaggcaaca  10080
ttaatcctca gcaagtgcaa tttgcagcca ttaaattgaa ctaactgata ctacaatgca  10140
atcagtatca acaagtggtt tggcttggaa gatggagtct aggggctcta caggagtagc  10200
tactctctaa tggagttgca ttttgaagca ggacactgtg aaaagctggc ctcctaaaga  10260
ggctgctaaa cattagggtc aattttccag tgcactttct gaagtgtctg cagttcccca  10320
tgcaaagctg cccaaacata gcacttccaa ttgaatacaa ttatatgcag gcgtactgct  10380
tcttgccagc actgtccttc tcaaatgaac tcaacaaaca atttcaaagt ctagtagaaa  10440
gtaacaagct ttgaatgtca ttaaaaagta tatctgcttt cagtagttca gcttatttat  10500
gcccactaga aacatcttgt acaagctgaa cactggggct ccagattagt ggtaaaacct  10560
actttataca atcatagaat catagaatgg cctgggttgg aagggacccc aaggatcatg  10620
aagatccaac acccccgcca caggcagggc caccaacctc cagatctggt actagaccag  10680
gcagcccagg gctccatcca acctggccat gaacacctcc agggatggag catccacaac  10740
ctctctgggc agcctgtgcc agcacctcac caccctctct gtgaagaact ttccctgac   10800
atccaatcta agccttccct ccttgaggtt agatccactc ccccttgtgc tatcactgtc  10860
tactcttgta aaaagttgat tctcctcctt tttggaaggt tgcaatgagg tctccttgca  10920
gccttcttct cttctgcagg atgaacaagc ccagctccct cagcctgtct ttataggaga  10980
ggtgctccag ccctctgatc atctttgtgg ccctcctctg gacccgctcc aagagctcca  11040
catctttcct gtactggggg ccccaggcct gaatgcagta ctccagatgg ggcctcaaaa  11100
gagcagagta aagagggaca atcaccttcc tcaccctgct ggccagccct cttctgatgg  11160
agccctggat acaactggct ttctgagctg caacttctcc ttatcagttc cactattaaa  11220
acaggaacaa tacaacaggt gctgatggcc agtgcagagt ttttcacact tcttcatttc  11280
ggtagatctt agatgaggaa cgttgaagtt gtgcttctgc gtgtgcttct tcctcctcaa  11340
atactcctgc ctgatacctc accccacctg ccactgaatg gctccatggc cccctgcagc  11400
cagggccctg atgaacccgg cactgcttca gatgctgttt aatagcacag tatgaccaag  11460
ttgcacctat gaatacacaa acaatgtgtt gcatccttca gcacttgaga agaagagcca  11520
aatttgcatt gtcaggaaat ggtttagtaa ttctgccaat taaaacttgt ttatctacca  11580
tggctgtttt tatggctgtt agtagtggta cactgatgat gaacaatggc tatgcagtaa  11640
aatcaagact gtagatattg caacagacta taaaattcct ctgtggctta gccaatgtgg  11700
```

```
tacttcccac attgtataag aaatttggca agtttagagc aatgtttgaa gtgttgggaa    11760
atttctgtat actcaagagg gcgtttttga caactgtaga acagaggaat caaaaggggg    11820
tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
taggg                                                                11945

<210> SEQ ID NO 68
<211> LENGTH: 285
<212> TYPE: DNA
<213> ORGANISM: SV40
<220> FEATURE:
<221> NAME/KEY: misc_feature
<222> LOCATION: (1)..(285)
<223> OTHER INFORMATION: SV40 Polyadenylation Sequence

<400> SEQUENCE: 68
aaagtctaga gtcggggcgg ccggccgctt cgagcagaca tgataagata cattgatgag      60
tttggacaaa ccacaactag aatgcagtga aaaaaatgct ttatttgtga aatttgtgat     120
gctattgctt tatttgtaac cattataagc tgcaataaac aagttaacaa caacaattgc     180
attcatttta tgtttcaggt tcagggggag gtgtgggagg ttttttaaag caagtaaaac     240
ctctacaaat gtggtaaaat cgataaggat ccgtcgagcg gccgc                     285
```